US008524659B2

(12) United States Patent
Cheng et al.

(10) Patent No.: US 8,524,659 B2
(45) Date of Patent: Sep. 3, 2013

(54) RNA VIRUS-DERIVED PEPTIDES WITH MODIFIED SIDE CHAINS

(75) Inventors: Richard Ping Cheng, Taipei (TW); Cheng-Hsun Wu, Taipei (TW); Ming-Huei Weng, Taipei (TW); Li-Min Huang, Taipei (TW)

(73) Assignee: National Taiwan University, Taipei (TW)

( * ) Notice: Subject to any disclaimer, the term of this patent is extended or adjusted under 35 U.S.C. 154(b) by 0 days.

(21) Appl. No.: 13/440,101

(22) Filed: Apr. 5, 2012

(65) Prior Publication Data

US 2013/0109618 A1    May 2, 2013

(30) Foreign Application Priority Data

Nov. 2, 2011   (TW) .................................. 100139918

(51) Int. Cl.
*A01N 37/18*     (2006.01)
*A61K 38/00*    (2006.01)
*A61P 31/12*    (2006.01)

(52) U.S. Cl.
USPC .......................................................... 514/3.7

(58) Field of Classification Search
None
See application file for complete search history.

(56) References Cited

U.S. PATENT DOCUMENTS 6,495,663 B1 *  12/2002  Rothbard et al. ............. 530/329
2003/0077289 A1 *  4/2003  Wang ......................... 424/185.1

OTHER PUBLICATIONS

Ohyama et al., J. Biochem., 1979, 86, 11-16.*

* cited by examiner

*Primary Examiner* — Marcela M Cordero Garcia
*Assistant Examiner* — Kaipeen Yang
(74) *Attorney, Agent, or Firm* — Bacon & Thomas, PLLC

(57) ABSTRACT

The present invention provides a RNA virus-derived peptides with modified side chains, wherein the side chains of the RNA virus-derived peptide are modified by altering the side-chain length or charges thereof such that the RNA virus-derived peptide has a high binding affinity for viral RNA and an high cellular uptake capability. The present invention also provides a composition for inhibiting RNA virus wherein the RNA virus-derived peptide can effectively inhibit viral self-replication and treat related diseases by its high affinity for viral RNA. A drug delivery carrier is also provided, wherein the RNA virus-derived peptides can carry desired drugs to the intracellular target due to its cellular uptake capability and thereby enhances the drug-delivery and treating efficiency.

11 Claims, 11 Drawing Sheets

7μM

30μM

RNA VIRUS-DERIVED PEPTIDES WITH MODIFIED SIDE CHAINS

FIELD OF THE INVENTION

The present invention relates a RNA virus-derived peptide with modified side chains. In particular, the present invention relates a peptide, wherein the binding affinity for viral RNAs and the cellular uptake capability are regulated by altering the side-chain properties such as length or charges thereof.

BACKGROUND OF THE INVENTION

Tat(47-57) is the 11-amino acid basic region of HIV Tat protein (human immunodeficiency virus transactivator of transcription protein, residues 47-57) which interacts with the transactivator response element (TAR) RNA, and is responsible for cell penetration. The Tat-TAR interaction is crucial for HIV proliferation, whereas the cell penetration capability of Tat is important for inducing viral proliferation in infected neighboring cells and inducing apoptosis of nearby healthy immune cells. Since the six Arg residues in this short basic region of Tat are critical for both TAR RNA recognition and cell penetration, Tat(47-57) would be an attractive system to simultaneously study the effect of Arg side chain length on two distinct bioactivities.

For example, U.S. Pat. No. 7,056,656 disclosed a Tat derived oligourea which competes with the Tat molecule of the TAR RNA in HIV-1 for the specificity to inhibit protein-nucleic acid interactions.

U.S. Patent Application No. US2009/0047272 A1 disclosed an antiviral composition, comprising a nuclease covalently attached to a target ligand (Tb)r to the inhibit the viral function by cleaving viral nucleic acids, wherein the target ligand (Tb)r may be a membrane permeating peptide comprising Arg/Lys-rich peptide, which may be selected from a peptide of YGRKKRPQRRR (SEQ ID NO: 20, HIV TAT47-57).

However, above-mentioned prior arts failed to regulate both biological activity of Tat peptide-TAR RNA recognition and cellular uptake activity, resulting in a Tat peptide having a high affinity for RNAs but probably losing its uptake ability, and vice versa. Thus, Tat(47-57) related drugs, which can effectively inhibit the replication of RNA virus (e.g. HIV virus), have not been found yet in the market.

SUMMARY OF THE INVENTION

Based on these defects in prior art, developing and improving is necessary. Thus, an objective of the present invention provided herein is a RNA virus-derived peptide with modified side chains, and thus the binding affinity between the peptide and viral RNAs can be regulated by altering the side-chain length or charges to modify this peptide such that the peptide can effectively bind with various RNA viruses.

Another objective of the present invention provided herein is a method for using the RNA virus-derived peptide, whereby a composition for inhibiting RNA virus can be prepared, and thus the viral self-replication can be effectively inhibited by the high affinity between the RNA virus-derived peptide and viral RNA.

A further objective of the present invention provided herein is a RNA virus-derived peptide with modified side chains and the use thereof, wherein the cellular uptake capability is regulated by altering the side-chain properties such as length or charges thereof such that the RNA virus-derived peptide may be used as a drug delivery carrier.

For these objectives, a RNA virus-derived peptide with modified side chains is provided herein, including the formula (I):

wherein the $n_1$, $n_2$, $n_3$, $n_4$, $n_5$ and $n_6$ may be a positive integer no greater than 8, respectively;

X is NH or O

Y, Y' and Y'' may be any amino acid side chain group, respectively; and the $n_1$, $n_2$, $n_3$, $n_4$, $n_5$ and $n_6$ are not 3 at the same time when X is NH.

In a preferred embodiment, the $n_1$, $n_2$, $n_3$, $n_4$, $n_5$ and $n_6$ may be 3 respectively when X is O.

In another preferred embodiment, the RNA virus-derived peptide may be a HIV virus-derived peptide. Preferably, the HIV virus-derived peptide may be a Tat(47-57) derived peptide.

In another preferred embodiment, the RNA virus-derived peptide may be Tyr-Gly-Agb-Lys-Lys-Agb-Agb-Gln-Agb-Agb-Agb-NH$_2$ (SEQ ID NO: 1), wherein the Agb may be (S)-2-amino-4-guanidinobutyric acid.

In another preferred embodiment, the RNA virus-derived peptide may be Tyr-Gly-Agh-Lys-Lys-Agh-Agh-Gln-Agh-Agh-Agh-NH$_2$ (SEQ ID NO: 2), wherein the Agh may be (S)-2-amino-6-guanidinohexanoic acid.

In a preferred embodiment, the $n_1$, $n_2$, $n_3$, $n_4$, $n_5$ and $n_6$ may be 2 respectively.

In another preferred embodiment, the $n_1$, $n_2$, $n_3$, $n_4$, $n_5$ and $n_6$ may be 4 respectively.

A method for preparing a composition for inhibiting RNA virus using a RNA virus-derived peptide with modified side chains is also provided herein, wherein the RNA virus-derived peptide may include the above-mentioned formula (I).

In a preferred embodiment, the $n_1, n_2, n_3, n_4, n_5$ and $n_6$ may be an integer of 1 to 4 respectively, and the $n_1, n_2, n_3, n_4, n_5$ and $n_6$ are not 3 at the same time.

The present invention further provides a method for preparing a drug delivery carrier using a RNA virus-derived peptide with modified side chains, wherein the RNA virus-derived peptide may include the above-mentioned formula (I).

In a preferred embodiment, $n_1, n_2, n_3, n_4, n_5$ or $n_6$ may be an integer of 1 to 8 respectively, and the $n_1, n_2, n_3, n_4, n_5$ and $n_6$ are not 3 at the same time.

A composition for inhibiting RNA virus is further provided, including:

the RNA virus-derived peptide with modified side chains, and a pharmaceutically acceptable adjuvant.

In a preferred, the composition may be applied individually, wherein a high binding affinity of the RNA virus-derived peptide with modified side chains may be used to inhibit viral self-replication such that RNA related diseases will be treated effectively. In another preferred embodiment, the composition may further include a drug, which may be used in combination with the RNA virus-derived peptide.

A drug delivery carrier prepared by the RNA virus-derived peptide is also provided.

In describing and claiming the invention, the following terminology will be used in accordance with the definitions set forth below to be considered illustrative, and shall not be restricted or limited by the foregoing detailed description.

The term "peptide" is used herein to refer to a chain of two or more amino acids or amino acid analogues (including non-naturally occurring amino acids), with adjacent amino acids joined by peptide (—NHCO—) bonds. Thus, the peptides of the invention include oligopeptides, polypeptides, proteins, mimetopes and peptidomimetics.

As used herein, the term "amino acid" is defined as alpha amino acids, encompassing any molecule containing both amino and carboxyl functional groups. The amino acids encompassed in the present invention may include either the L or D form of the amino acid, or a racemic mixture. Moreover, the amino acids can be naturally-occurring and non-naturally occurring amino acids. Thus, a peptide of the present invention can be made from genetically encoded amino acids, naturally occurring non-genetically encoded amino acids, or synthetic amino acids.

As used herein, the term "composition" includes at least one active ingredient of the RNA virus-derived peptide, one or more pharmaceutically acceptable adjuvant(s), and optionally other therapeutic agent(s). The composition may further bind other drugs to be used in combination with the active ingredient, and thereby enhance the treatment effect.

The term "adjuvant" is used herein to include any of pharmaceutically acceptable ingredient, which may be compatible with other ingredients and innocuous to the desired target, including: acidifying agents, additives, adsorbents, aerosol propellants, air displacement agents, alkalizing agents, anticaking agents, anticoagulants, antimicrobial preservatives, antioxidants, antiseptics, bases, binders, buffering agents, chelating agents, coating agents, coloring agents, desiccants, detergents, diluents, disinfectants, disintegrants, dispersing agents, dissolution enhancing agents, dyes, emollients, emulsifying agents, emulsion stabilizers, fillers, film forming agents, flavor enhancers, flavoring agents, flow enhancers, gelling agents, granulating agents, humectants, lubricants, mucoadhesives, ointment bases, ointments, oleaginous vehicles, organic bases, pastille bases, pigments, plasticizers, polishing agents, preservatives, sequestering agents, skin penetrants, solubilizing agents, solvents, stabilizing agents, suppository bases, surface active agents, surfactants, suspending agents, sweetening agents, therapeutic agents, thickening agents, tonicity agents, toxicity agents, viscosity-increasing agents, water-absorbing agents, water-miscible cosolvents, water softeners, or wetting agents or the like.

As used herein, the drug delivery "carrier" refers to transport substances capable of delivering therapeutical agents or diagnostic agents to target cells. In the present invention, a complex may be formed by combining the present RNA virus-derived peptide and therapeutical agents or diagnostic agents, whereby these agents may be delivered using the cellular uptake property of the RNA virus-derived peptide.

DETAILED DESCRIPTION OF THE PREFERRED EMBODIMENT

Figure 1:
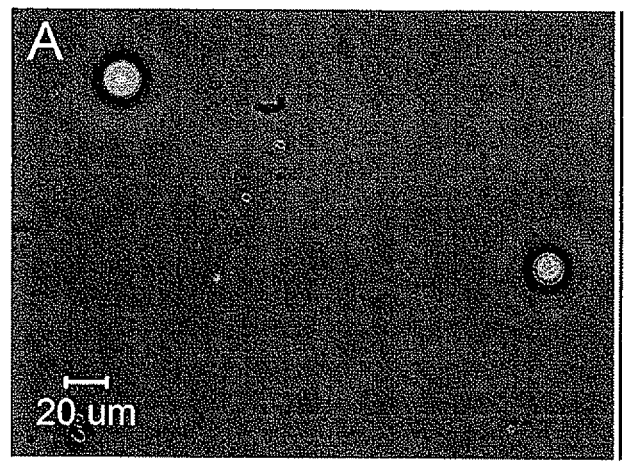
FIG. 1 illustrated the overlaid bright-field and fluorescence microscopy images of Jurkat cells incubated with 7 μM Flu-AghTat (panel A), Flu-ArgTat (panel B), Flu-AgbTat (panel C) for 15 minutes at 37° C. in the presence of fetal bovine serum, washed and treated with trypsin at 37° C. for 5 minutes.
Figure 1:
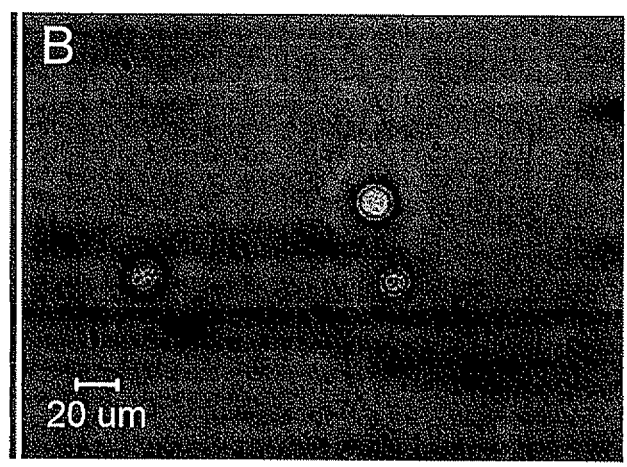
Figure 1:
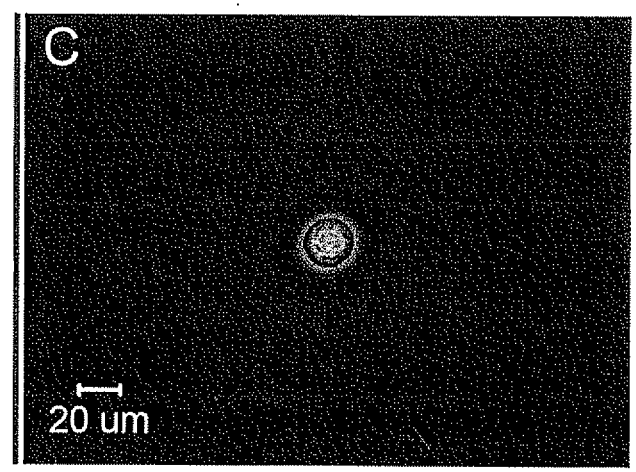

Preferred embodiments of the present invention will be described below in more detail with reference to the accompanying drawings. The present invention may, however, be embodied in different forms and should not be constructed as limited to the embodiments set forth herein. Other objectives, advantages, and novel features of the invention will become more apparent from the following detailed description when taken in conjunction with the accompanying drawings.

Example 1

Modifying all Arginine Side-Chain Length in Tat(47-57) Derived Peptides to Observe Effects on Both RNA Binding Specificity and Cellular Uptake Capability Material and Method All of the chemical reagents except those indicated otherwise were purchased from Aldrich. Diisopropylethylamine (DIEA), piperidine, trifluoroacetic acid (TFA), acetic anhydride, N-methyl-N-(trimethylsilyl)trifluoroacetamide, Tween-20, and acetic anhydride were from Acros. Guanidine hydrochloride was from Fluka. Dimethylformamide (DMF), ethyl acetate, dichloromethane (DCM) and hexane were from Mallinckrodt. Methanol and acetonitrile were from Merck. Ammonium persulfate and 1,4-Dioxane were from J. T. Baker. Glycerol, boric acid, bis-acrylamide, Tris-HCl, and tris(hydroxylmethyl)-aminomethane (Tris) were from Bioshop. Organic and high performance liquid chromatography (HPLC) solvents were from Merck Taiwan. N-9-Fluorenylmethoxycarbonyl (Fmoc)-amino acids, 1-hydroxybenzotriazole (HOBO, and O-1H-benzotriazol-1-yl-1,1,3,3-tetra-methyl uronium hexafluorophosphate (HBTU) were from Novabiochem, Fmoc-PAL-PEG-PS resin was from Applied Biosystems. Reagents and solvents were used without further purification. Analytical reverse phase (RP)-HPLC was performed on an Agilent 1200 series chromatography system using a Vydac $C_{18}$ column (4.6 mm diameter, 250 mm length). Preparative RP-HPLC was performed on a Waters Breeze chromatography system using a Vydac $C_4$ and $C_{18}$ columns (22 mm diameter, 250 mm length). Mass spectrometry of the peptides was performed on a matrix-assisted laser desorption ionization time-of-flight (MALDI-TOF) spectrometer (Bruker Daltonics Biflex IV) using α-cyano-4-hydroxycinnamic acid as the matrix. Determination of peptide concentration was performed on a UV-Vis spectrophotometer (Jasco V-650). Circular dichroism (CD) spectra were collected on a J815 spectrometer using 1 mm pathlength cell. The CD data was reported in mean residue molar ellipticity (deg·cm$^2$·dmol$^{-1}$). The gel shift results were imaged using a Typhoon TRIO$^+$ gel imager with the emission wavelength set at 526 nm. Fluorescence intensity was acquired on a Varian Cary Eclipse fluorescence spectrophotometer. Cells were incubated using a $CO_2$ incubator (Thermo Scientific, Form a steri-cycle $CO_2$ incubaor). Cells were counted using a hemacytometer (Reichert Bright-Line, hemacytometer 1490). The fluorescence intensity of 6-carboxy-fluorescein labeled Tat peptides was measured on a flow cytometer (Becton Dickinson, FACS Canto™ II) and the peptide-treated Jurkat cells were imaged using a inverted fluorescence microscope (Olympus, IX71).

The preparation of N,N-Bis(tert-butoxycarbonyl)-guanidine

The synthesis was performed according to published procedures, as described in (a) Cheng, R. P. W., Y.-J.; Wang, W.-R.; Koyack, M. J.; Suzuki, Y.; Wu, C.-H.; Yang, P.-A.; Hsu, H.-C.; Kuo, H.-T.; Girinath, P.; Fang, C.-J. Amino Acids 2011, in press; (b) Feichtinger, K.; Sings, H. L.; Baker, T. J.; Matthews, K.; Goodman, M. J. Org. Chem. 1998, 63, 8432-8439; (c) Feichtinger, K.; Zapf, C.; Sings, H. L.; Goodman, M. J. Org. Chem. 1998, 63, 3804-3805, which is incorporated herein by reference. 1,4-Dioxane (30 mL) was added to a solution of guanidine hydrochloride (2.8727 g, 30.049 mmol) and sodium hydroxide (4.9573 g, 123.9 mmol) in water (30 mL), the mixture was cooled to 0° C. using an ice water bath. Di-tert-butyl-dicarbonate (14.5296 g, 66.1302 mmol) was then added to the reaction, and the residual was washed into the reaction with another 30 mL of 1,4-dioxane. The reaction was allowed to warm to room temperature and stirred for 3 days. The reaction mixture was then concentrated under reduced pressure to dryness. The resulting white emulsion was diluted with water (60 mL) and extracted with ethyl acetate (3×60 mL). The organic layer was then extracted with 10% citric acid (60 mL), water (60 mL), and brine (60 mL) and dried over anhydrous sodium sulfate. Finally, the dried organic solution was then concentrated under reduced pressure to obtain the desired product as a white powder (5.4 g, 69.2% yield). $^1$H NMR (400 MHz, CDCl$_3$) 3.46 (s, 1H), 1.46 (s, 18H); ESI-MS calculated for $C_{11}H_{21}N_3O_4$ [MH+]=260.3, observed [MH+]=260.1.

The preparation of N,N'-Di-Boc-N"-trifluoromethanesulfonyl-guanidine

The synthesis was performed according to published procedures, as described in "The preparation of N,N-Bis(tert-butoxycarbonyl)-guanidine". A solution of N,N-bis(tert-butoxycarbonyl)-guanidine (3.0414 g, 12.035 mmole) and triethylamine (2.0 mL) in anhydrous dichloromethane (60 mL) was cooled to −68° C. using a dry ice/acetone bath under an atmosphere of nitrogen. Triflic anhydride (2.1 mL, 12.590 mmole) was added dropwise (2.1 mL/30 minutes). After half of the triflic anhydride was added, the color became light brown and the reaction mixture was allowed to warm to room temperature and stirred overnight. The reaction was washed with 2 M sodium bisulfate (20 mL) and water (20 mL), and then dried over anhydrous sodium sulfate. The dry organic solution was concentrated under reduced pressure and purified by chromatography on silica gel eluted with $CH_2Cl_2$ to obtained the desired product (3.1 g, 64.8%). $^1$H NMR (400 MHz, CDCl$_3$) 1.51 (s, 18H); ESI-MS calculated for $C_{12}H_{20}F_3N_3O_6S$ [MNa+]=414.4, observed [MNa+]=414.2.

The preparation of N$^\alpha$-Fmoc-(S)-2-amino-N$^{\omega,\omega'}$-di(Boc)-6-guanidinohexanoic acid (Fmoc-Agh(Boc)$_2$-OH)

The synthesis was performed following published procedures, as described in Cheng, R. P. W., Y.-J.; Wang, W.-R.; Koyack, M. J.; Suzuki, Y.; Wu, C.-H.; Yang, P.-A.; Hsu, H.-C.; Kuo, H.-T.; Girinath, P.; Fang, C.-J. Amino Acids 2011, in press, which is incorporated herein by reference. Fmoc-Lys-OH (1.100 g, 2.98 mmol) was suspended in anhydrous dichloromethane (6 mL) under nitrogen. N-Methyl-N-(trimethylsilyl)trifluoroacetamide (1.2 mL, 6.60 mmol) was added, and then the reaction mixture was heated to reflux until a clear solution was formed. The solution was cooled to room temperature, and N,N'-di-Boc-N"-trifluoromethanesulfonylguanidine (1.410 g, 3.60 mmol) was added followed by triethylamine (504 μL, 3.60 mmol). The reaction mixture was stirred at room temperature, and the reaction was monitored by TLC. Upon completion, the reaction mixture was diluted with dichloromethane (6 mL) and washed with 2 M sodium bisulfate and water, and dried with sodium sulfate. The dried organic solution was then concentrated under reduced pressure and purified by flash chromatography on silica gel ($CH_2Cl_2$ to 95:5 $CH_2Cl_2$/methanol) to obtain the desired product as a white powder (1.347 g, 73.8% yield). $R_f$=0.17

(95:5 CH$_2$Cl$_2$/methanol); m.p. 85-88° C.; [α]$^{25}_D$=16.9 (0.0099 g mL$^{-1}$ CHCl$_3$); $^1$H NMR (500 MHz, CDCl$_3$/TMS): δ=8.439 (s, 1H), 7.749-7.257 (m, 8H), 5.638 (d, J (H,H)= 7.324 Hz, 1H), 4.371 (d, J (H,H)=5.798 Hz, 1H), 4.505 (br s, 1H), 4.371 (d, J (H,H)=5.798 Hz, 1H), 4.204 (t, J (H,H)=6.867 Hz, 1H), 3.406 (m, 1H), 3.310 (m, 1H), 1.918 (m, 1H), 1779 (m, 1H), 1.479 (s, 9H), 1.471 (s, 9H), 1.647-1.277 ppm (m, 6H); $^{13}$C NMR (75 MHz, CDCl$_3$/TMS): δ=175.416, 163.388, 156.764, 156.604, 153.759, 144.425, 144.289, 141.830, 128.217, 127.602, 125.659, 120.477, 83.924, 80.395, 67.609, 54.064, 47.713, 41.187, 32.172, 29.008, 28.719, 28.567, 22.755 ppm; IR (liquid): ν bar=3226, 2983, 1720, 1617, 1512, 1450, 1416, 1368, 1335, 1137, 1054 cm$^{-1}$; ESI-MS calculated for C$_{32}$H$_{42}$N$_4$O$_8$ [MH$^+$]: 611.3075, observed: 611.1; HRMS calculated for C$_{32}$H$_{42}$N$_4$O$_8$ [MH$^+$]: 611.3075, observed: 611.3063.

Peptide Synthesis

Fmoc-PAL-PEG-PS (0.05 mmol) was swollen in N,N-dimethylformamide (DMF, 5 mL) for 30 minutes. The resin was then deprotected by 20% piperidine/DMF (3×8 min) and rinsed with DMF (5×1 min). A mixture of 3 equivalents of the appropriately protected Fmoc amino acid, HOBt and HBTU was dissolved in DMF (1 mL). Diisopropylethylamine (DIEA, 8 equivalents) was then added to the solution and mixed thoroughly. The solution was then applied to the resin. The vial that contained the solution was rinsed with DMF (1 mL) and added to the reaction. The first coupling was carried out for 8 hours. The 8th to 14th residues were coupled for 1.5 hours. Other residues were coupled for 45 minutes. After each coupling, the resin was washed with DMF (5×1 min). The resin was subsequently washed with DMF (5×1 min) and methanol, and was lyophilized.

Solid phase guanidinylation was performed to synthesize Agb- and Agp-containing peptides. For Agb-containing peptides, the corresponding Dab(ivDde)-containing peptide was synthesized first. The resin was treated with trityl chloride to protect the fluorescein moiety. Then the ivDde protecting group was removed by suspending the resin in 2% hydrazine in DMF (4 mL, 5×8 min) and shaking at room temperature. The resin was washed with DMF (4 mL, 5×1.5 min) and lyophilized. For Agp-containing peptides, the corresponding Dap(Mtt)-containing peptide was synthesized first. The Mtt protecting group was then removed by suspending the resin in 1% CF$_3$COOH in CH$_2$Cl$_2$ (4 mL, 15×3 min) and shaking at room temperature. Deprotection was continued until the filtrate no longer appeared yellow. The resin was washed with CH$_2$Cl$_2$ (4 mL, 5×1.5 min) and lyophilized. After removal of orthogonal protecting groups from the resin-bound protected peptides, the resin was resuspended in a solution of N,N'-di-Boc-N''-trifluoromethanesulfonylguanidine (820.9 mg, 2 mmol) and Et$_3$N (480 μL, 6.5 mmol) in CH$_2$Cl$_2$. The reaction was shaken at room temperature. The reaction was microwaved once every hour (3×7 sec, 30% power). Reaction was monitored by cleaving a small amount (about 5 mg) of peptide-bound resin and analyzed by RP-HPLC.

Peptides were deprotected and cleaved off the resin by treating the resin with 95:5 trifluoroacetic acid (950 μL)/triisopropylsilane (50 μL) and shaken for 2 hours. The solution was then filtered through glass wool and the resin was washed with TFA (3×1 mL). The combined filtrate was evaporated by a gentle stream of N$_2$. The resulting material was washed with hexanes, dissolved in water, and lyophilized. The peptide (1 mg mL$^{-1}$ aqueous solution) was analyzed using analytical RP-HPLC on a C18 column with a flow rate of 1 mL min$^{-1}$, temperature 25° C., linear 1% min$^{-1}$ gradient from 100% A to 0% A (solvent A: 99.9% water, 0.1% TFA; solvent B: 90% acetonitrile, 10% water, 0.1% TFA). Appropriate linear solvent A/solvent B gradients were used for purification on preparative RP-HPLC on C$_4$ and C$_{18}$ column. The identity of the peptide was confirmed by MALDI-TOF.

The Peptide Preparation Example 1

AghTat(Ac-Tyr-Gly-Agh-Lys-Lys-Agh-Agh-Gln-Agh-Agh-Agh-NH$_2$) (i.e. n$_1$, n$_2$, n$_3$, n$_4$, n$_5$ and n$_6$ of formula (I) were 4 respectively; SEQ ID NO.: 2)

The peptide was synthesized using 242.4 mg (0.05090 mmol) of Fmoc-PAL-PEG-PS resin. The synthesis gave 349.1 mg (66.6% yield). The cleavage yielded 119.4 mg of crude peptide (>99%). The peptide was purified by preparative RP-HPLC using C4 and C18 columns to 98.5% purity, using linear gradients PLG00_06 and PLG01_11, respectively. Retention time on analytical RP-HPLC was 17.0 minutes. The identity of the peptide was confirmed by MALDI-TOF mass spectrometry. Calculated for C$_{72}$H$_{133}$N$_{33}$O$_{14}$ [MH]$^+$: 1684.07; observed m/z: 1684.938.

The Peptide Preparation Example 2

ArgTat(Ac-Tyr-Gly-Arg-Lys-Lys-Arg-Arg-Gln-Arg-Arg-Arg-NH$_2$) (a naturally-occurring Tat-derived peptide; i.e. n$_1$, n$_2$, n$_3$, n$_4$, n$_5$ and n$_6$ of formula (I) were 3, respectively; SEQ ID NO.: 3)

The naturally-occurring Tat-derived peptide was obtained by capping a Tat(47-57) peptide (-Tyr-Gly-Arg-Lys-Lys-Arg-Arg-Gln-Arg-Arg-Arg-(SEQ ID NO.: 4)) at both termini and synthesized by the following method:

The peptide was synthesized using 234.9 mg (0.0433 mmol) of Fmoc-PAL-PEG-PS resin. The synthesis gave 334.0 mg (59.6% yield). The cleavage yielded 116.8 mg of crude peptide (>99%). The peptide was purified by preparative RP-HPLC using C4 and C18 columns to 98.7% purity, using linear gradients PLG00_05 and PLG04_16, respectively. Retention time on analytical RP-HPLC was 15.4 minutes. The identity of the peptide was confirmed by MALDI-TOF mass spectrometry. Calculated for C$_{72}$H$_{133}$N$_{33}$O$_{14}$ [MH]$^+$: 1599.98; observed m/z: 1600.34.

The Peptide Preparation Example 3

AgbTat(Ac-Tyr-Gly-Agb-Lys-Lys-Agb-Agb-Gln-Agb-Agb-Agb-NH$_2$) (i.e. n$_1$, n$_2$, n$_3$, n$_4$, n$_5$ and n$_6$ of formula (I) were 2, respectively; SEQ ID NO.: 1)

The peptide was synthesized using 245.3 mg (0.05151 mmol) of Fmoc-PAL-PEG-PS resin. The synthesis gave 327.5 mg (53.6% yield). The cleavage yielded 87.0 mg of crude peptide (>99%). The peptide was purified by preparative RP-HPLC using a C4 and C18 columns to 99.0% purity, using linear gradients PLG00_05 and PLG03_14, respectively. Retention time on analytical RP-HPLC was 15.0 minutes. The identity of the peptide was confirmed by MALDI-TOF mass spectrometry. Calculated for C$_{60}$H$_{110}$N$_{33}$O$_{14}$ [MH]$^+$: 1516.89; observed m/z: 1516.72.

The Peptide Preparation Example 4

Flu-AghTat

```
Flu-AghTat
(6-carboxyfluorescein-βAla-Tyr-Gly-Agh-Lys-Lys-
Agh-Agh-Gln-Agh-Agh-Agh-NH2; SEQ ID NO.: 4)
```

The peptide was synthesized using 245.8 mg (0.0516 mmol) of Fmoc-PAL-PEG-PS resin. The synthesis gave 340.6 mg (52.0% yield). The cleavage yielded 122.1 mg of crude peptide (>99%). The peptide was purified by preparative RP-HPLC using C4 and C18 columns to 98.6% purity, using linear gradients PLG04_13 and PLG16_26, respectively. Retention time on analytical RP-HPLC was 26.2 minutes. The identity of the peptide was confirmed by MALDI-TOF mass spectrometry. Calculated for $C_{94}H_{146}N_{34}O_{20}$ $[MH]^+$: 2072.15; observed m/z: 2071.98.

The Peptide Preparation Example 5

```
Flu-ArgTat(6-carboxyfluorescein-βAla-Tyr-Gly-Arg-
Lys-Lys-Arg-Arg-Gln-Arg-Arg-Arg-NH2; SEQ ID NO.: 5)
```

The peptide was synthesized using 144.6 mg (0.0305 mmol) of Fmoc-PAL-PEG-PS resin. The synthesis gave 200.1 mg (48.3% yield). The cleavage yielded 47.5 mg of crude peptide (>99%). The peptide was purified by preparative RP-HPLC using C4 and C18 columns to 99.2% purity, using linear gradients PLG06_13 and PLG13_26, respectively. Retention time on analytical RP-HPLC was 25.7 minutes. The identity of the peptide was confirmed by MALDI-TOF mass spectrometry. Calculated for $C_{88}H_{134}N_{34}O_{20}$ $[MH]^+$: 1987.051; observed m/z: 1987.114.

The Peptide Preparation Example 6

```
Flu-AgbTat
(6-carboxyfluorescein-βAla-Tyr-Gly-Agb-Lys-Lys-
Agb-Agb-Gln-Agb-Agb-Agb-NH2; SEQ ID NO.: 6).
```

The peptide was synthesized using 247.8 mg (0.05203 mmol) of Fmoc-PAL-PEG-PS resin. The synthesis gave 329.7 mg (46.5% yield). The cleavage yielded 136.2 mg of crude peptide (>99%). The peptide was purified by preparative RP-HPLC using C4 and C18 columns to 96.1% purity, using linear gradients PLG03_12 and PLG14_25, respectively. Retention time on analytical RP-HPLC was 27.5 minutes. The identity of the peptide was confirmed by MALDI-TOF mass spectrometry. Calculated for $C_{82}H_{123}N_{34}O_{20}$ $[MH]^+$: 1903.96; observed m/z: 1902.39.

Peptide Concentration Determination by UV-Vis Spectroscopy

The concentration of the XaaTat peptide stock solutions was determined using the Edelhoch method (The Xaa herein was Agh, Arg or Agb, respectively). A 10 mM solution was prepared for each XaaTat peptide based on weight. The UV data was collected using a 1 mm pathlength cell. The concentration of XaaTat peptide stock solutions was determined by the tyrosine absorbance in 6 M guanidinium chloride ($\epsilon_{282}$=1220, $\epsilon_{280}$=1285, $\epsilon_{278}$=1395, $\epsilon_{276}$=1455). The UV absorbance was collected at wavelengths 276, 278, 280, and 282 nm over 1 minute (60×1 sec) to accurately determine the concentration of the sample. The concentration of the peptide solutions was derived using Kaleidagraph 3.52 (Synergy Software, CA).

A 7 mM solution was prepared for each Flu-XaaTat peptide based on weight (The Xaa herein was Agh, Arg or Agb, respectively). The UV data was collected using a 1 mm pathlength cell. The concentration of Flu-XaaTat peptide stock solutions was determined in pH 9 buffer (1 mM sodium phosphate, 1 mM sodium citrate, and 1 mM sodium borate) based on the absorbance of 6-carboxyfluorescein ($\epsilon_{492}$=81000). The UV absorbance was collected at 492 nm over 1 minute (60×1 sec) to accurately determine the concentration of the sample. Based on the Beer-Lambert law, the concentration of the peptide solutions was derived using Kaleidagraph 3.52 (Synergy Software, CA).

Fluorescence Anisotropy

The binding affinity of XaaTat peptides (Xaa=Agh, Arg and Agb) for TAR RNA was measured by fluorescence anisotropy using a Varian Cary Eclipse fluorescence spectrophotometer. The anisotropy (r) was calculated using the following equation:

$$R = \frac{I_{VV} - I_{VH} \times \frac{I_{HV}}{I_{HH}}}{I_{VV} + 2\left(I_{VH} \times \frac{I_{HV}}{I_{HH}}\right)}$$

where $I_{vv}$, $I_{vh}$, $I_{hh}$, $I_{hv}$ are the fluorescence intensities with the excitation polarizer and emission polarizer is oriented perpendicular ($I_{vh}$ and $I_{hv}$) and parallel ($I_{vv}$ and $I_{hh}$) to the direction of the polarized excitation. The fluorescein-labeled TAR RNA (F-TAR-RNA) was excited at 490 nm and the polarized emissions were monitored at 512 nm. The slits were set at 10 nm for both excitation and emission. The integration time was 20 seconds. All data were measured in a Sub-Micro (Starna Cell, Inc.) with a starting volume of 160 μL. Each addition (1 μL) of XaaTat was equilibrated for two minutes before the fluorescence signal was recorded. All experiments were performed at room temperature in TKT buffer (TKT: 50 mM Tris-HCl, pH 7.4, 20 mM KCl and 0.02% Tween20). The initial concentration of F-TAR-RNA was 25 nM. The TKT solution and peptide stock solution were both equilibrated at room temperature more than 20 minutes before the experiment. The experiment was repeated three times independently. For every single point, three measurements were performed and the average value was used for deriving the apparent (apparent $K_D$). The apparent for the peptide-RNA complex was derived by fitting the data assuming a 1:1 peptide-RNA stoichiometry. The fitting was performed using Kaleidagraph 3.52. (Synergy Software, CA).

Gel Shift Assay

The fluorescein-labeled TAR RNA (F-TAR-RNA) was purchased from Sigma. F-TAR-RNA was dissolved in diethyl pyrocarbonate treated $H_2O$ to give a 50 μM solution. Binding assays were performed at room temperature. Peptide and RNA were incubated in pH 7.4 buffer (10 μL) containing Tris-HCl (50 mM), KCl (50 mM), poly-dIdC (10 μg/mL), 2% glycerol, and Triton X-100 (0.05%). The F-TAR-RNA concentration was 100 nM. The samples were analyzed by loading into 12% native polyacrylamide gels in 0.5% TB buffer and electrophoresis was performed with 140 V at room temperature. Dried gels were scanned by the Typhoon TRIO+ Variable Mode Imager. Bands corresponding to the free and bound RNA were quantified using ImageQuant software. The apparent dissociation constants were globally derived from the quantified data assuming a 1:1 binding stoichiometry.

Fluorescence Microscope of Live Jurkat Cells

Live Jurkat cells (8×10$^5$ cells) were incubated with 7 μM Flu-XaaTat for 15 minutes at 37° C. in RPMI medium with fetal bovine serum. After incubation, the suspension was centrifuged at 2200 rpm. The cells were washed with phosphate buffered saline (137 mM NaCl, 2.7 mM KCl, 10 mM sodium phosphate dibasic, 2 mM potassium phosphate monobasic, pH 7.4) twice to remove extracellular peptide. To ensure removal of any surface-bound peptide, cells were then incubated with 0.05% trypsin at 37° C. for 5 minutes, washed with PBS twice. Finally, cells were resuspended in 500 μL PBS containing 1 μg/mL propidium iodide. The cells were then examined by a fluorescence microscope (Olympus IX71) (492/517 nm; excitation/observation).

Cellular Uptake Assay

All apparatuses were sterilized by autoclave sterilizer, and the experimental surfaces were wiped with 70% ethanol. All operations were performed in a laminar flow hood. The number of cells was determined by a hemacytometer. There were 9 squares with 1.0 mm$^2$ area and 0.1 mm depth in the hemacytometer. The number of cells in the four corner squares was counted and averaged. The average was multiplied by $10^4$ to obtain the number of cells in a 1 mL suspension. The cellular uptake experiments were performed using $8 \times 10^5$ cells. Jurkat cells were incubated with the peptides at various concentrations (7, 30, 60, and 120 μM) at 37° C. with 5% $CO_2$ for 15 minutes. The cells were then washed with PBS (2 g/L KCl, 2 g/L $KH_2PO_4$, 80 g/L NaCl, 11.5 g/L $Na_2PO_4$) (2×400 μL) to remove the fetal bovine serum which might interfere with the proteolytic activity of trypsin. The cells were then incubated with 0.05% trypsin/EDTA in PBS for 5 minutes to remove the peptides which adhered to the cell surface rather than entry to the cell. The cells were washed with PBS (2×400 μL). The cells were then resuspended in 500λ PBS and transferred into the flow tube. The cells were terminated by adding Triton-X 100 to give the dead control group. Propidium iodide (PI) was added to all samples to stain the dead cells but should not stain the live cells. Fluorescence analysis for the Jurkat cells was performed with a flow cytometer (FACScan, Becton Dickinson Bioscience). The voltage of the photomultiplier tube for forward scatter, side scatter and propidium iodide was set to 270, 470, and 350, respectively. Live cells containing appropriate forward scatter and side scatter values were selected and gated as the P1 region for normal and live cells in the live control group. The minimum propidium iodide fluorescence intensity for the dead cells treated with propidium iodide in the P1 region was set as the threshold value for dead cells. In other words, cells with propidium iodide fluorescence below the threshold value would be deemed live cells. The fluorescence of 6-carboxyfluorescein was considered when the cell morphology was in the P1 region and the propidium iodide fluorescence intensity was lower than the threshold value. The 6-carboxyfluorescein fluorescence intensity was acquired for 10,000 events at room temperature. The data presented are the mean fluorescence intensity for the 10,000 cells. Each experiment was independently repeated at least three times.

MTT Assay for Determining Cell Survival

The cells were grown to appropriate cell density (roughly $2 \times 10^6$ cells/mL) and transferred into new media one day before performing the experiment. For each assay, $8 \times 10^5$ cells as determined by a hemocytometer were added into an eppendorf. The cells were centrifuged at 2200 rpm for 5 minutes. The supernatant was removed by suction. Then 200 μL of 7 μM or 30 μM XaaTat peptide was added. The cells were incubated for 4 hours at 37° C. and then centrifuged at 2200 rpm for 5 minutes. The cells were washed with RPMI medium twice, and then 200 μL of 0.5 mg/mL MTT in serum free RPMI buffer was added and incubated at 37° C. for 3.5 hours. The cells were then centrifuged at 4000 rpm for 5 minutes. The supernatant was then transferred to two wells (100 μL each) of a 96-well plate. Then 400 μL DMSO was added to the cells in the assaying eppendorf. The eppendorf was then vortexed for 5 minutes to solubilize the MTT purple crystals, and centrifuged at 2200 rpm for 5 minutes. Then the supernatant was transferred to 4 wells (100 μL each) of the 96-well plate for analysis. The absorbance at 570 was determined for each well using a microplate reader with the absorbance at 655 nm used for background correction. A standard curve was generated using different number of cells ($8 \times 10^5$, $4 \times 10^5$ and $2 \times 10^5$). The absorbance for each sample for each peptide at each concentration was then correlated to the number of live cells based on the standard curve.

Results

1. Results of RNA Binding Specificity

The naturally-occurring Tat(47-57) was capped at both termini to give peptide ArgTat. All six Arg residues were replaced with Agh (one methylene longer than Arg) and Agb (one methylene shorter than Arg) to give peptides AghTat and AgbTat, respectively. To enable the detection of cellular uptake, the peptides were capped with fluorescein at the N-terminus. All peptides were synthesized by solid phase peptide synthesis using Fmoc-based chemistry, purified by reverse phase high performance liquid chromatography to greater than 95% purity, and confirmed by matrix assisted laser desorption ionization mass spectrometry.

The effect of Arg side-chain length on RNA recognition for XaaTat (Xaa=Agh, Arg and Agb) peptides was investigated in the absence and presence of poly(dI-dC) by fluorescence anisotropy and electrophoretic mobility shift assays (EMSA) (See Table 1), respectively. The HIV TAR RNA was labeled with fluorescein at the 3'-terminus to enable these experiments. The apparent dissociation constants ($K_D$) were derived from the experimental data, suggesting that the smaller $K_D$ is, the stronger the binding affinity is.

Table 1 showed that the binding affinity of AghTat and TAR-RNA and that of AgbTat and TAR-RNA had no apparent difference compared with the binding affinity of naturally-occurring derived ArgTat and TAR-RNA in the absence and presence of poly(dI-dC). This result suggested that RNA virus-derived peptides with modified side chains (AghTat and AgbTat) also have the excellent binding affinity for TAR-RNA.

Moreover, to determine the specificity for peptides to TAR RNA, the strength of the binding affinity was determined in the presence of competing negatively charged poly(dI-dC). The binding affinity of AghTat was significantly reduced upon adding poly(dI-dC) in Table 1, whereas the affinity of ArgTat and TAR RNA was somewhat affected by the presence of poly-anionic poly(dI-dC). Surprisingly, the affinity of AgbTat was not affected by the presence of poly(dI-dC). That is, AgbTat had the better binding specificity for TAR RNA. These results suggested that altering the Arg side-chain length did not affect the affinity between Tat peptides and TAR-RNA, but affects specificity between them.

TABLE 1

Apparent dissociation constants ($K_D$) for the binding of Xaa-Tat (Xaa = Agh, Arg and Agb) with HIV TAR RNA in the absence and presence of poly(dI-dC)

| Peptide | Apparent $K_D$ [nM][a] | |
|---|---|---|
| | HIV TAR RNA[b] | HIV TAR RNA with poly(dI-dC)[c] |
| AghTat | 36 ± 9 | 450 ± 40 |
| ArgTat | 25 ± 3 | 67 ± 19 |
| AgbTat | 32 ± 9 | 31 ± 9 |

[a]The apparent dissociation constants were derived from the experimental data assuming a 1:1 binding stoichiometry.
[b]Values determined by fluorescence anisotropy experiments. The experiments were performed by titrating the peptide into 25 nM fluorescein-labeled HIV TAR RNA.
[c]Values determined by electrophoretic mobility shift assays (EMSA). The assays were performed with 100 nM fluorescein-labeled HIV TAR RNA, varying amounts of peptide, in the presence of 10 μg/mL poly(dI-dC).

2. Results of Cellular Uptake Experiments

Cellular uptake experiments were performed on Jurkat cells, because these cells belonged to a CD4+ helper T cell cancer cell line which was the target of HIV. Jurkat cells were incubated separately with various concentration (7, 30, 60, 120 μM) of Flu-XaaTat for 15 minutes at 37° C. in the presence of fetal bovine serum, and then treated with trypsin to remove cell-surface bound peptide.

FIG. 1 illustrated the overlaid bright-field and fluorescence microscopy images of Jurkat cells incubated with 7 μM Flu-AghTat (panel A), Flu-ArgTat (panel B), Flu-AgbTat (panel C) for 15 minutes at 37° C. in the presence of fetal bovine serum, washed and treated with trypsin at 37° C. for 5 minutes. Obvious cellular uptake for all three peptides was shown in FIG. 1.

Figure 2:
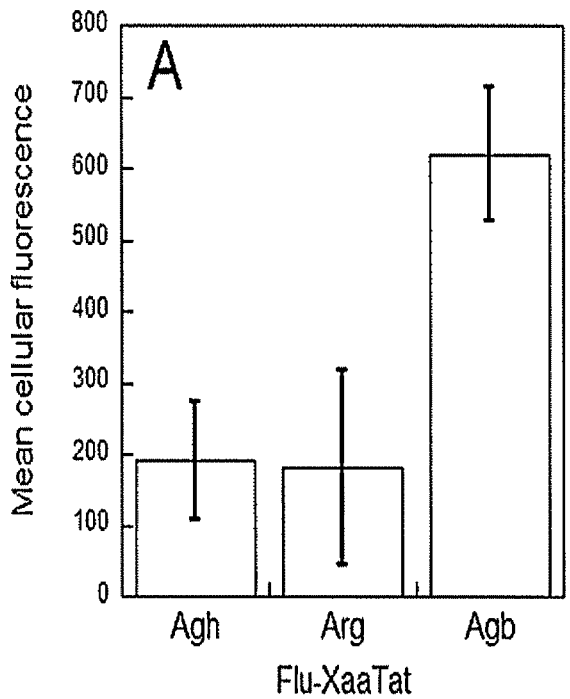
FIG. 2 illustrated Flow cytometry results for cellular uptake of Flu-XaaTat peptides into Jurkat cells in the presence of fetal bovine serum at 37° C. Panel A: mean cellular fluorescence upon incubation with 7 μM peptide for 15 minutes. Panel B: mean cellular fluorescence upon incubation with various peptide concentrations (7, 30, 60, 120 μM) for 15 minutes.
Figure 2:
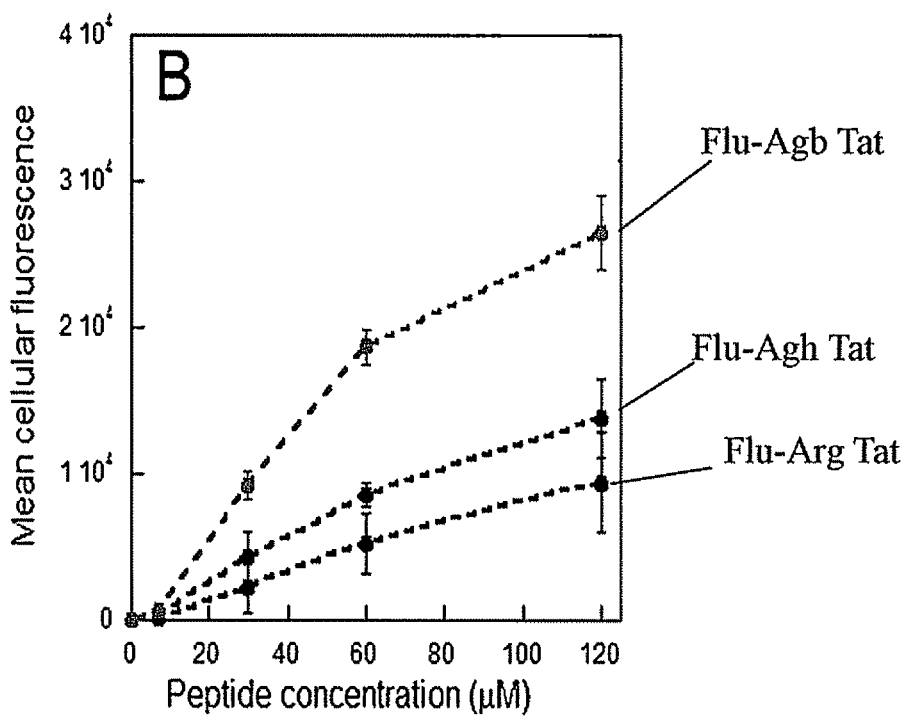

Cellular uptake was then investigated quantitatively using flow cytometry. FIG. 2 illustrated Flow cytometry results for cellular uptake of Flu-XaaTat peptides into Jurkat cells in the presence of fetal bovine serum at 37° C., wherein Panel A: mean cellular fluorescence upon incubation with 7 μM peptide for 15 minutes. Panel B: mean cellular fluorescence upon incubation with various peptide concentrations (7, 30, 60, 120 μM) for 15 minutes. Incubating with 7 μM peptide, Flu-AgbTat exhibited 3 times higher uptake into cells compared to Flu-ArgTat and Flu-AghTat (FIG. 2A). The better uptake of the Agb-containing peptide was also present at higher peptide concentrations (FIG. 2B). Meanwhile, Flu-AghTat exhibited more cellular uptake compared to Flu-ArgTat at concentrations higher than 7 μM.

Figure 3:
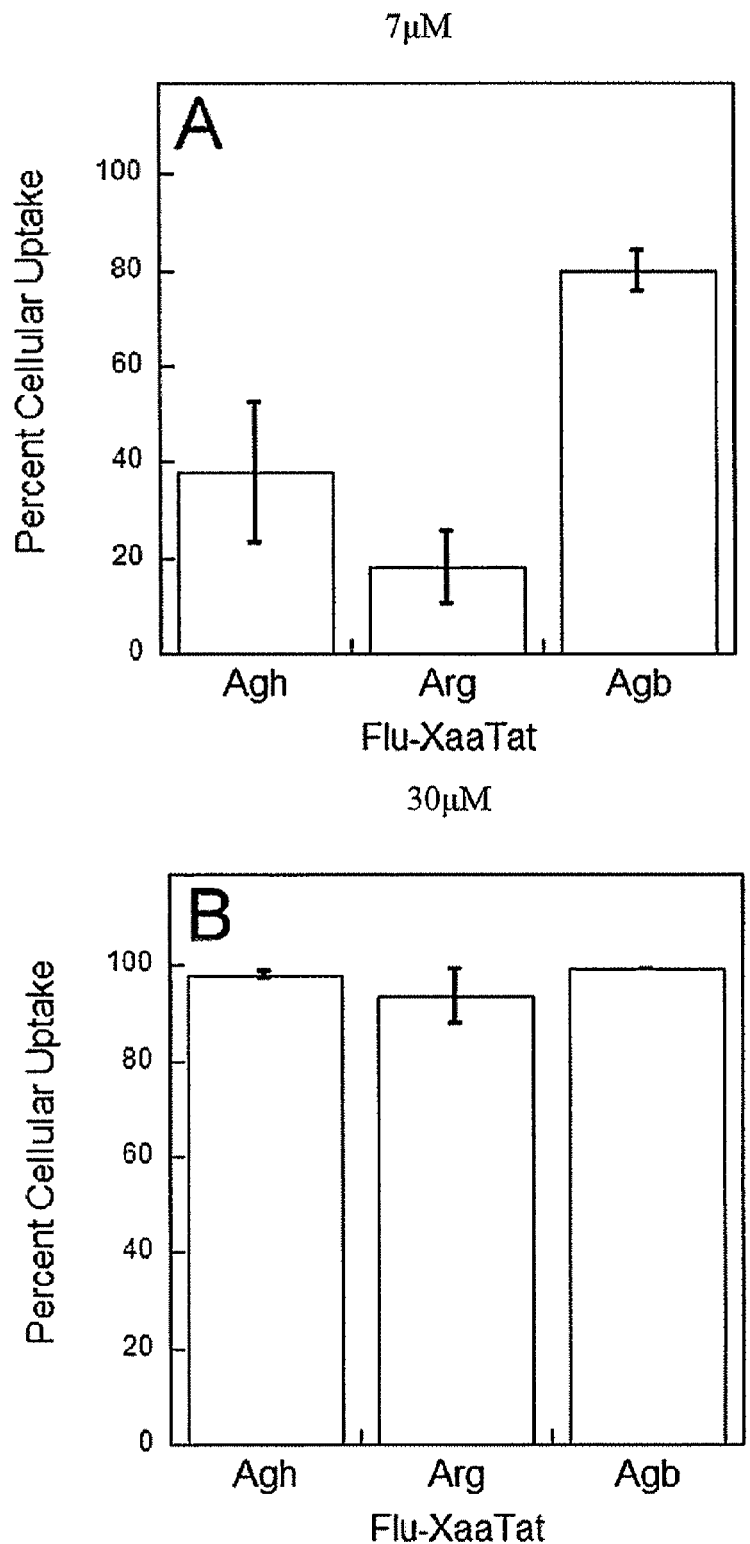
FIG. 3 illustrated Mean percent cellular uptake of Flu-XaaTat peptides into Jurkat cells in the presence of fetal bovine serum with 7 μM (panel A) and 30 μM (panel B) peptide for 15 minutes at 37° C.

FIG. 3 illustrated Mean percent cellular uptake of Flu-XaaTat peptides into Jurkat cells in the presence of fetal bovine serum with 7 μM (panel A) and 30 μM (panel B) peptide for 15 minutes at 37° C. More than 70% of the cells showed uptake upon shortening the Arg side chain length by one methylene to Agb (FIG. 3A); this is up to four times the number of cells with uptake compared to the Arg peptide. On the other hand, nearly all cells exhibited peptide uptake upon raising the peptide concentration to 30 μM regardless of side chain length (FIG. 3B).

FIGS. 2 and 3 demonstrated that both modified Flu-AgbTat and Flu-AghTat exhibited cellular uptake, which could be increased by changing Arg side-chain length in Tat(47-57). Especially when the Arg side-chain length was shortened by one methylene to Agb, it exhibited an excellent effect on uptake.

3. Results of Cytotoxicity Experiments

Figure 4:
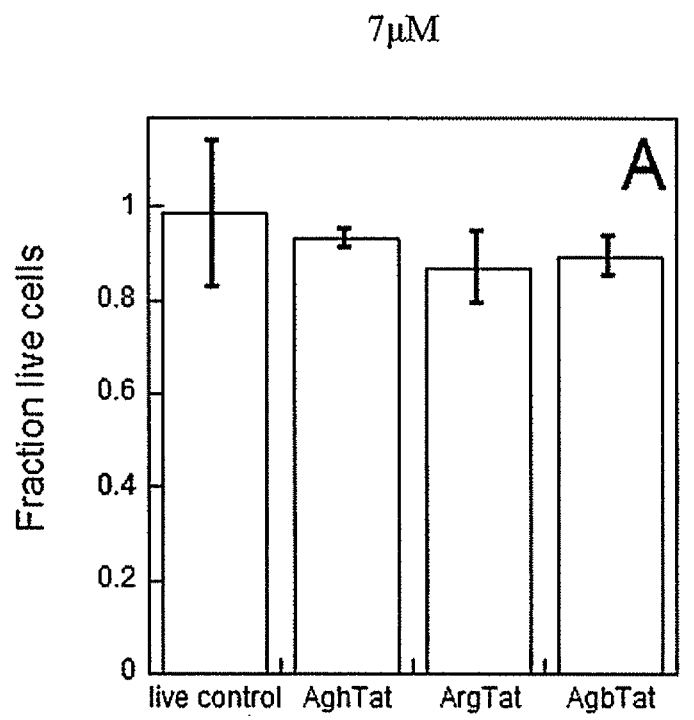
FIG. 4 illustrated that cell survival results upon exposure to 7 μM (panel A) and 30 μM (panel B) peptide AghTat, ArgTat, and AgbTat for 4 hours determined by MTT assays.
Figure 4:
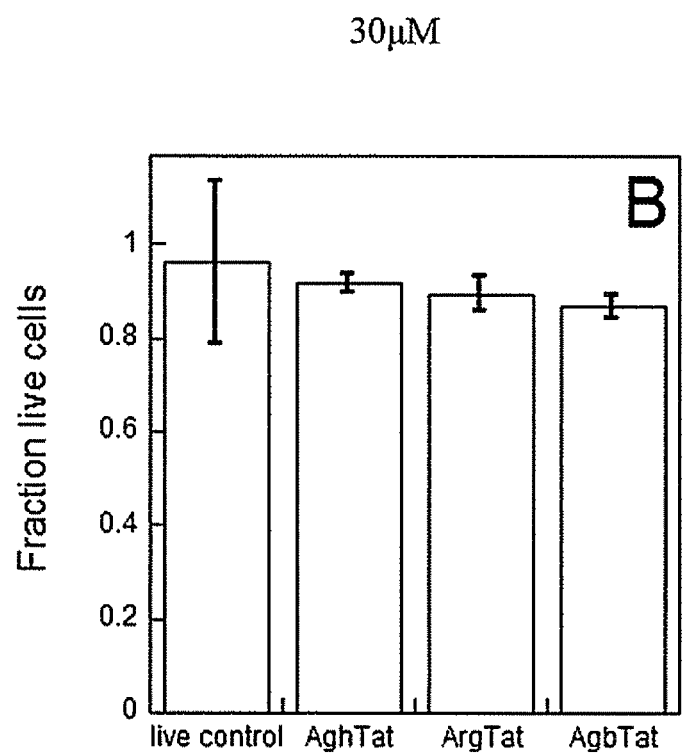

FIG. 4 illustrated that cell survival results upon exposure to 7 μM (panel A) and 30 μM (panel B) peptide AghTat, ArgTat, and AgbTat for 4 hours at 37° C. as determined by MTT assays. These results in FIG. 4 showed that all AghTat, ArgTat and AgbTat had minimal cytotoxicity as the increasing peptide concentration. For example, 30 μM of the Agb-containing peptide had great RNA binding specificity and cellular uptake activity. Further, MTT assays on Jurkat cells showed minimal cytotoxicity upon exposure to 30 μM of the Agb-containing peptide for 4 hours at 37° C., but further studies were still needed for the development of anti-HIV therapeutics or drug delivery applications. Furthermore, these results demonstrated that altering the Arg side-chain length affects both RNA binding specificity and cellular uptake activity of Tat-derived peptides, and should be a useful strategy for developing molecules with bio-medical applications.

Example 2

Modifying Each Arginine Side-Chain Charges in Tat(47-57) Derived Peptides (i.e. Replacing $NH_2$ Groups in Arg with O Atom) Respectively to Observe Effects on Both RNA Binding Specificity and Cellular Uptake Capability

The Peptide Preparation Example 1

Tat-Cit49 (Ac-Tyr-Gly-Cit-Lys-Lys-Arg-Arg-Gln-Arg-Arg-Arg-$NH_2$; SEQ ID NO.: 7)

The corresponding Fmoc-Tat-Cit49 peptide (SEQ ID NO: 21, Fmoc-Tyr-Gly-Cit-Lys-Lys-Arg-Arg-Gln-Arg-Arg-Arg-$NH_2$) was synthesized using 0.2404 g (0.0505 mmol) Fmoc-PAL-PEG-PS. The synthesis gave 0.3256 g of resin (51.1% yield). Retention time on analytical RP-HPLC was 31.51 minutes. The identity of the peptide was confirmed by MALDI-TOF MS. Calculated for [MH$^+$] $C_{79}H_{128}N_{32}O_{16}$ [1782.02]; observed [1780.63]. The Fmoc group on Fmoc-Tat-Cit49 was removed selectively using 20% piperidine/DMF (5 mL, 3×8 mins). Then the resin was reacted with a solution of acetic anhydride (95 μL, 20 equivalents) and DIEA (125 μL, 20 equivalents) for 2 hours. The synthesis gave 0.3205 g of resin (50.6% yield). The cleavage yielded 102.4 mg of crude peptide (>99% yield). The peptide was purified by preparative RP-HPLC using $C_4$ (PLG00_04) and $C_{18}$ (PLG02_14) columns to 98.0% purity (14.9 mg). Retention time on analytical RP-HPLC was 16.18 minutes. The identity of the peptide was confirmed by MALDI-TOF MS. Calculated for [MH$^+$] $C_{66}H_{120}N_{32}O_{15}$ [1601.97]; observed [1601.32].

The Peptide Preparation Example 2

Tat-Cit52 (Ac-Tyr-Gly-Arg-Lys-Lys-Cit-Arg-Gln-Arg-Arg-Arg-$NH_2$; SEQ ID NO.: 8)

The corresponding Fmoc-Tat-Cit52 peptide (SEQ ID NO: 22, Fmoc-Tyr-Gly-Arg-Lys-Lys-Cit-Arg-Gln-Arg-Arg-Arg-$NH_2$) was synthesized using 0.2678 g (0.0500 mmol) Fmoc-PAL-PEG-PS. The synthesis gave 0.3713 g of resin (62.6% yield). Retention time on analytical RP-HPLC was 31.03 minutes. The identity of the peptide was confirmed by MALDI-TOF MS. Calculated for [MH$^+$] $C_{79}H_{128}N_{32}O_{16}$ [1782.02]; observed [1780.96]. The Fmoc group on Fmoc-Tat-Cit52 was removed selectively using 20% piperidine/DMF (5 mL, 3×8 mins). Then the resin was reacted with a solution of acetic anhydride (95 μL, 20 equivalents) and DIEA (125 μL, 20 equivalents) for 2 hours. The synthesis gave 0.3651 g of resin (61.7% yield). The cleavage yielded 104.0 mg of crude peptide (>99% yield). The peptide was purified by preparative RP-HPLC using $C_4$ (PLG00_04) and $C_{18}$ (PLG02_14) columns to 98.2% purity (12.3 mg). Reten tion time on analytical RP-HPLC was 15.77 minutes. The identity of the peptide was confirmed by MALDI-TOF MS. Calculated for [MH$^+$] C$_{66}$H$_{120}$N$_{32}$O$_{15}$ [1601.97]; observed [1601.64].

The Peptide Preparation Example 3

Tat-Cit53(Ac-Tyr-Gly-Arg-Lys-Lys-Arg-Cit-Gln-Arg-Arg-Arg-NH$_2$; SEQ ID NO.: 9)

The corresponding Fmoc-Tat-Cit53 peptide (SEQ ID NO: 23, Fmoc-Tyr-Gly-Arg-Lys-Lys-Arg-Cit-Gln-Arg-Arg-Arg-NH$_2$) was synthesized using 0.2987 g (0.0508 mmol) Fmoc-PAL-PEG-PS. The synthesis gave 0.4090 g of resin (65.7% yield). Retention time on analytical RP-HPLC was 31.28 minutes. The identity of the peptide was confirmed by MALDI-TOF MS. Calculated for [MH$^+$] C$_{79}$H$_{128}$N$_{32}$O$_{16}$ [1782.02]; observed [1780.57]. The Fmoc group on Fmoc-Tat-Cit53 was removed selectively using 20% piperidine/DMF (5 mL, 3×8 mins). Then the resin was reacted with a solution of acetic anhydride (95 µL, 20 equivalents) and DIEA (125 µL, 20 equivalents) for 2 hours. The synthesis gave 0.4026 g of resin (64.3% yield). The cleavage yielded 112.9 mg of crude peptide (>99% yield). The peptide was purified by preparative RP-HPLC using C$_4$ (PLG00__04) and C$_{18}$ (PLG02__14) columns to 97.3% purity (11.7 mg). Retention time on analytical RP-HPLC was 15.97 minutes. The identity of the peptide was confirmed by MALDI-TOF MS. Calculated for [MH$^+$] C$_{66}$H$_{120}$N$_{32}$O$_{15}$ [1601.97]; observed [1601.48].

The Peptide Preparation Example 4

Tat-Cit55(Ac-Tyr-Gly-Arg-Lys-Lys-Arg-Arg-Gln-Cit-Arg-Arg-NH$_2$; SEQ ID NO.:10)

The corresponding Fmoc-Tat-Cit55 peptide (SEQ ID NO: 24, Fmoc-Tyr-Gly-Arg-Lys-Lys-Arg-Arg-Gln-Cit-Arg-Arg-NH$_2$) was synthesized using 0.2918 g (0.0496 mmol) Fmoc-PAL-PEG-PS. The synthesis gave 0.3950 g of resin (63.0% yield). Retention time on analytical RP-HPLC was 33.99 minutes. The identity of the peptide was confirmed by MALDI-TOF MS. Calculated for [MH$^+$] C$_{79}$H$_{128}$N$_{32}$O$_{16}$ [1782.02]; observed [1782.98]. The Fmoc group on Fmoc-Tat-Cit55 was removed selectively using 20% piperidine/DMF (5 mL, 3×8 mins). Then the resin was reacted with a solution of acetic anhydride (95 µL, 20 equivalents) and DIEA (125 µL, 20 equivalents) for 2 hours. The synthesis gave 0.3966 g of resin (65.6% yield). The cleavage yielded 152.8 mg of crude peptide (>99% yield). The peptide was purified by preparative RP-HPLC using C$_4$ (PLG00__04) and C$_{18}$ (PLG02__14) columns to 97.1% purity (7.6 mg). Retention time on analytical RP-HPLC was 16.07 minutes. The identity of the peptide was confirmed by MALDI-TOF MS. Calculated for [MH$^+$] C$_{66}$H$_{120}$N$_{32}$O$_{15}$ [1601.97]; observed [1601.80].

The Peptide Preparation Example 5

Tat-Cit56(Ac-Tyr-Gly-Arg-Lys-Lys-Arg-Arg-Gln-Arg-Cit-Arg-NH$_2$; SEQ ID NO.: 11)

The corresponding Fmoc-Tat-Cit56 peptide (SEQ ID NO: 25, Fmoc-Tyr-Gly-Arg-Lys-Lys-Arg-Arg-Gln-Arg-Cit-Arg-NH$_2$) was synthesized using 0.2983 g (0.0507 mmol) Fmoc-PAL-PEG-PS. The synthesis gave 0.4069 g of resin (64.9% yield). Retention time on analytical RP-HPLC was 33.82 minutes. The identity of the peptide was confirmed by MALDI-TOF MS. Calculated for [MH$^+$] C$_{79}$H$_{128}$N$_{32}$O$_{16}$ [1782.02]; observed [1783.39]. The Fmoc group on Fmoc-Tat-Cit56 was removed selectively using 20% piperidine/DMF (5 mL, 3×8 mins). Then the resin was reacted with a solution of acetic anhydride (95 µL, 20 equivalents) and DIEA (125 µL, 20 equivalents) for 2 hours. The synthesis gave 0.4002 g of resin (64.2% yield). The cleavage yielded 156.9 mg of crude peptide (>99% yield). The peptide was purified by preparative RP-HPLC using C$_4$ (PLG00__04) and C$_{18}$ (PLG02__14) columns to 96.2% purity (6.7 mg). Retention time on analytical RP-HPLC was 15.96 minutes. The identity of the peptide was confirmed by MALDI-TOF MS. Calculated for [MH$^+$] C$_{66}$H$_{120}$N$_{32}$O$_{15}$ [1601.97]; observed [1601.98].

The Peptide Preparation Example 6

Tat-Cit57(Ac-Tyr-Gly-Arg-Lys-Lys-Arg-Arg-Gln-Arg-Arg-Cit-NH$_2$; SEQ ID NO.: 12)

The corresponding Fmoc-Tat-Cit57 peptide (SEQ ID NO: 26, Fmoc-Tyr-Gly-Arg-Lys-Lys-Arg-Arg-Gln-Arg-Arg-Cit-NH$_2$) was synthesized using 0.2929 g (0.0498 mmol) Fmoc-PAL-PEG-PS. The synthesis gave 0.4103 g of resin (75.5% yield). Retention time on analytical RP-HPLC was 32.91 minutes. The identity of the peptide was confirmed by MALDI-TOF MS. Calculated for [MH$^+$] C$_{79}$H$_{128}$N$_{32}$O$_{16}$ [1782.02]; observed [1782.71]. The Fmoc group on Fmoc-Tat-Cit57 was removed selectively using 20% piperidine/DMF (5 mL, 3×8 mins). Then the resin was reacted with a solution of acetic anhydride (95 µL, 20 equivalents) and DIEA (125 µL, 20 equivalents) for 2 hours. The synthesis gave 0.4014 g of resin (65.3% yield). The cleavage yielded 101.5 mg of crude peptide (>99% yield). The peptide was purified by preparative RP-HPLC using C$_4$ (PLG00__04) and C$_{18}$ (PLG02__14) columns to 97.8% purity (11.8 mg). Retention time on analytical RP-HPLC was 16.16 minutes. The identity of the peptide was confirmed by MALDI-TOF MS. Calculated for [MH$^+$] C$_{66}$H$_{120}$N$_{32}$O$_{15}$ [1601.97]; observed [1602.18].

The above-mentioned prepared peptides were further tested by Fluorescence Anisotropy and Gel Shift Assay according to the same protocols as mentioned in the above Example 1.

The Synthesis of Cell Penetration Peptide

The resin (Fmoc-PAL-PEG-PS) was swollen in DMF with shaking for 30 minutes. The resin was washed with DMF (5 mL, 5×1.5 min). The Fmoc group was deprotected by 20% piperidine/DMF (5 mL, 3×8 min) and the resin was rinsed with DMF (5 mL, 5×1.5 min). The mixture of the appropriate protected amino acid (3 equivalents), HOBT (3 equivalents), and HBTU (3 equivalents) was dissolved in 1 mL DMF and DIEA (12 equivalents), and then applied to the resin. The vial was washed with DMF (2×1 mL) and applied to the resin and shaken. The coupling time depended on the kind (β-branch) and location of amino acid. Arginine was triple coupled, 25 minutes each time. The first amino acid was coupled for 8 hours, residues 2~7 for 75 minutes, residues 8-15 for 90 minutes. When the coupling was complete, the resin was washed with DMF and deblocked as described earlier. A mixture of 6-carboxy-fluorescein (3 equivalents), HOBT (3 equivalents), and HBTU (3 equivalents) was dissolved in 1 mL DMF and DIEA (12 equivalents) and applied to the resin. The resin was shaken for 3 hours and washed with DMF (5 mL, 5×1.5 min). The resin was washed with DMF (5 mL, 5×1.5 min), methanol (5 mL), and was lyophilized overnight. Peptides was deprotected and cleaved off the resin using TFA (5 mL), triisopropylsilane (250 µL), and ethyl 1,2-dithiol (250 µL), and shaken for 2 hours. The reaction was filtered through glass wool, and washed with TFA (3×3 mL). The combined filtrate was evaporated by a gentle stream of $N_2$. The residual material was washed with hexanes (3×3 mL), dissolved in water and lyophilized. The peptide was analyzed by analytical HPLC equipped with a 250 mm length $C_{18}$ column using 1 mL/min flow rate, linear 1%/min gradient from 100% A to 0% A (solvent A: 99.9% water, 0.1% TFA; solvent B: 90% acetonitrile, 10% water, 0.1% TFA), and confirmed by MALDI-TOF MS. Different linear gradients (solvent A: 99.9% water, 0.1% TFA; solvent B: 90% acetonitrile, 10% water, 0.1% TFA) were chosen to purify each peptide by preparative RP-HPLC equipped with either a $C_4$ or $C_{18}$ column using 10 mL/min flow rate, linear 0.5%/min gradient.

The Peptide Preparation Example 1

6CF-Tat-Cit49(6CF-βAla-Tyr-Gly-Cit-Lys-Lys-Arg-Arg-Gln-Arg-Arg-Arg-NH$_2$; SEQ ID NO.: 13)

The corresponding Fmoc-Tat-Cit49 peptide (SEQ ID NO: 27, Fmoc-Tyr-Gly-Cit-Lys-Lys-Arg-Arg-Gln-Arg-Arg-Arg-NH$_2$) was synthesized using 0.2218 g (0.0466 mmol) Fmoc-PAL-PEG-PS. The synthesis gave 0.3005 g of resin (51.1% yield). Retention time on analytical RP-HPLC was 31.51 minutes. The identity of the peptide was confirmed by MALDI-TOF MS. Calculated for [MH$^+$] $C_{79}H_{128}N_{32}O_{16}$ [1782.02]; observed [1780.63]. The Fmoc group on Fmoc-Tat-Cit49 was removed using 20% piperidine/DMF (5 mL, 3×8 mins). The resin was reacted with a mixture of β-alanine (3 equivalents), HOBT (3 equivalents), and HBTU (3 equivalents) for 1.5 hours. The resin was wash with DMF and deblocked as described earlier. The resin was reacted with a mixture of 6-carboxy-fluorescein (3 equivalents), HOBT (3 equivalents), and HBTU (3 equivalents) for 3 hours. The synthesis gave 0.2905 g of resin (30.5% yield). The cleavage yielded 139.7 mg of crude peptide (>99% yield). The peptide was purified by preparative RP-HPLC using $C_4$ (PLG02_12) and $C_{18}$ (PLG13_25) columns to 97.5% purity (7.4 mg). Retention time on analytical RP-HPLC was 27.2 minutes. The identity of the peptide was confirmed by MALDI-TOF MS. Calculated for [MH$^+$] $C_{88}H_{133}N_{33}O_{21}$ [1989.04]; observed [1988.76].

The Peptide Preparation Example 2

6CF-Tat-Cit52(6CF-βAla-Tyr-Gly-Arg-Lys-Lys-Cit-Arg-Gln-Arg-Arg-Arg-NH$_2$; SEQ ID NO.: 14)

The corresponding Fmoc-Tat-Cit52 peptide (SEQ ID NO: 28, Fmoc-Tyr-Gly-Arg-Lys-Lys-Cit-Arg-Gln-Arg-Arg-Arg-NH$_2$) was synthesized using 0.2496 g (0.0466 mmol) Fmoc-PAL-PEG-PS. The synthesis gave 0.3460 g of resin (62.6% yield). Retention time on analytical RP-HPLC was 31.03 minutes. The identity of the peptide was confirmed by MALDI-TOF MS. Calculated for [MH$^+$] $C_{79}H_{128}N_{32}O_{16}$ [1782.02]; observed [1780.92]. The Fmoc group on Fmoc-Tat-Cit52 was removed using 20% piperidine/DMF (5 mL, 3×8 mins). The resin was reacted with a mixture of β-alanine (3 equivalents), HOBT (3 equivalents), and HBTU (3 equivalents) for 1.5 hours. The resin was wash with DMF and deblocked as described earlier. The resin was reacted with a mixture of 6-carboxy-fluorescein (3 equivalents), HOBT (3 equivalents), and HBTU (3 equivalents) for 3 hours. The synthesis gave 0.3560 g of resin (53.4% yield). The cleavage yielded 145.8 mg of crude peptide (>99% yield). The peptide was purified by preparative RP-HPLC using $C_4$ (PLG02_12) and $C_{18}$ (PLG13_25) columns to 95.5% purity (5.3 mg). Retention time on analytical RP-HPLC was 27.3 minutes. The identity of the peptide was confirmed by MALDI-TOF MS. Calculated for [MH$^+$] $C_{88}H_{133}N_{33}O_{21}$ [1989.04]; observed [1988.85].

The Peptide Preparation Example 3

6CF-Tat-Cit53(6CF-βAla-Tyr-Gly-Arg-Lys-Lys-Arg-Cit-Gln-Arg-Arg-Arg-NH$_2$; SEQ ID NO.: 15)

The corresponding Fmoc-Tat-Cit53 peptide (SEQ ID NO: 29, Fmoc-Tyr-Gly-Arg-Lys-Lys-Arg-Cit-Gln-Arg-Arg-Arg-NH$_2$) was synthesized using 0.2776 g (0.0472 mmol) Fmoc-PAL-PEG-PS. The synthesis gave 0.3800 g of resin (65.7% yield). Retention time on analytical RP-HPLC was 31.28 minutes. The identity of the peptide was confirmed by MALDI-TOF MS. Calculated for [MH$^+$] $C_{79}H_{128}N_{32}O_{16}$ [1782.02]; observed [1780.57]. The Fmoc group on Fmoc-Tat-Cit53 was removed using 20% piperidine/DMF (5 mL, 3×8 mins). The resin was reacted with a mixture of β-alanine (3 equivalents), HOBT (3 equivalents), and HBTU (3 equivalents) for 1.5 hours. The resin was wash with DMF and deblocked as described earlier. The resin was reacted with a mixture of 6-carboxy-fluorescein (3 equivalents), HOBT (3 equivalents), and HBTU (3 equivalents) for 3 hours. The synthesis gave 0.3777 g of resin (46.6% yield). The cleavage yielded 76.8 mg of crude peptide (>99% yield). The peptide was purified by preparative RP-HPLC using $C_4$ (PLG02_12) and $C_{18}$ (PLG13_25) columns to 97.3% purity (2.8 mg). Retention time on analytical RP-HPLC was 27.5 minutes. The identity of the peptide was confirmed by MALDI-TOF MS. Calculated for [MH$^+$] $C_{88}H_{133}N_{33}O_{21}$ [1989.04]; observed [1988.91].

The Peptide Preparation Example 4

6CF-Tat-Cit55(6CF-βAla-Tyr-Gly-Arg-Lys-Lys-Arg-Arg-Gln-Cit-Arg-Arg-NH$_2$; SEQ ID NO.: 16)

The corresponding Fmoc-Tat-Cit55 peptide (SEQ ID NO: 30, Fmoc-Tyr-Gly-Arg-Lys-Lys-Arg-Arg-Gln-Cit-Arg-Arg- NH$_2$) was synthesized using 0.2982 g (0.0507 mmol) Fmoc-PAL-PEG-PS. The synthesis gave 0.4037 g of resin (63.0% yield). Retention time on analytical RP-HPLC was 33.99 minutes. The identity of the peptide was confirmed by MALDI-TOF MS. Calculated for [MH$^+$] C$_{79}$H$_{128}$N$_{32}$O$_{16}$ [1782.02]; observed [1782.98]. The Fmoc group on Fmoc-Tat-Cit55 was removed using 20% piperidine/DMF (5 mL, 3×8 mins). The resin was reacted with a mixture of β-alanine (3 equivalents), HOBT (3 equivalents), and HBTU (3 equivalents) for 1.5 hours. The resin was wash with DMF and deblocked as described earlier. The resin was reacted with a mixture of 6-carboxy-fluorescein (3 equivalents), HOBT (3 equivalents), and HBTU (3 equivalents) for 3 hours. The synthesis gave 0.3973 g of resin (57.5% yield). The cleavage yielded 95.7 mg of crude peptide (>99% yield). The peptide was purified by preparative RP-HPLC using C$_4$ (PLG02_12) and C$_{18}$ (PLG13_25) columns to 95.9% purity (4.8 mg). Retention time on analytical RP-HPLC was 27.2 minutes. The identity of the peptide was confirmed by MALDI-TOF MS. Calculated for [MH$^+$] C$_{88}$H$_{133}$N$_{33}$O$_{21}$ [1989.04]; observed [1988.91].

The Peptide Preparation Example 5

6CF-Tat-Cit56(6CF-βAla-Tyr-Gly-Arg-Lys-Lys-Arg-Arg-Gln-Arg-Cit-Arg-NH$_2$; SEQ ID NO.: 17)

The corresponding Fmoc-Tat-Cit56 peptide (SEQ ID NO: 31, Fmoc-Tyr-Gly-Arg-Lys-Lys-Arg-Arg-Gln-Arg-Cit-Arg-NH$_2$) was synthesized using 0.2988 g (0.0508 mmol) Fmoc-PAL-PEG-PS. The synthesis gave 0.4078 g of resin (64.9% yield). Retention time on analytical RP-HPLC was 33.82 minutes. The identity of the peptide was confirmed by MALDI-TOF MS. Calculated for [MH$^+$] C$_{79}$H$_{128}$N$_{32}$O$_{16}$ [1782.02]; observed [1783.39]. The Fmoc group on Fmoc-Tat-Cit56 was removed using 20% piperidine/DMF (5 mL, 3×8 mins). The resin was reacted with a mixture of β-alanine (3 equivalents), HOBT (3 equivalents), and HBTU (3 equivalents) for 1.5 hours. The resin was wash with DMF and deblocked as described earlier. The resin was reacted with a mixture of 6-carboxy-fluorescein (3 equivalents), HOBT (3 equivalents), and HBTU (3 equivalents) for 3 hours. The synthesis gave 0.4130 g of resin (64.2% yield). The cleavage yielded 183.1 mg of crude peptide (>99% yield). The peptide was purified by preparative RP-HPLC using C$_4$ (PLG02_12) and C$_{18}$ (PLG13_25) columns to 96.4% purity (7.0 mg). Retention time on analytical RP-HPLC was 27.1 minutes. The identity of the peptide was confirmed by MALDI-TOF MS. Calculated for [MH$^+$] C$_{88}$H$_{133}$N$_{33}$O$_{21}$ [1989.04]; observed [1988.95].

The Peptide Preparation Example 6

6CF-Tat-Cit57(6CF-βAla-Tyr-Gly-Arg-Lys-Lys-Arg-Arg-Gln-Arg-Arg-Cit-NH$_2$; SEQ ID NO.: 18)

The corresponding Fmoc-Tat-Cit57 peptide (SEQ ID NO: 32, Fmoc-Tyr-Gly-Arg-Lys-Lys-Arg-Arg-Gln-Arg-Arg-Cit-NH$_2$) was synthesized using 0.3070 g (0.0522 mmol) Fmoc-PAL-PEG-PS. The synthesis gave 0.4371 g of resin (75.5% yield). Retention time on analytical RP-HPLC was 32.91 minutes. The identity of the peptide was confirmed by MALDI-TOF MS. Calculated for [MH$^+$] C$_{79}$H$_{128}$N$_{32}$O$_{16}$ [1782.02]; observed [1782.71]. The Fmoc group on Fmoc-Tat-Cit57 was removed using 20% piperidine/DMF (5 mL, 3×8 mins). The resin was reacted with a mixture of β-alanine (3 equivalents), HOBT (3 equivalents), and HBTU (3 equivalents) for 1.5 hours. The resin was wash with DMF and deblocked as described earlier. The resin was reacted with a mixture of 6-carboxy-fluorescein (3 equivalents), HOBT (3 equivalents), and HBTU (3 equivalents) for 3 hours. The synthesis gave 0.4247 g of resin (68.0% yield). The cleavage yielded 180.0 mg of crude peptide (>99% yield). The peptide was purified by preparative RP-HPLC using C$_4$ (PLG02_12) and C$_{18}$ (PLG13_25) columns to 96.4% purity (7.0 mg). Retention time on analytical RP-HPLC was 27.1 minutes. The identity of the peptide was confirmed by MALDI-TOF MS. Calculated for [MH$^+$] C$_{88}$H$_{133}$N$_{33}$O$_{21}$ [1989.04]; observed [1988.88].

The above-mentioned prepared peptides were further tested by Fluorescence Microscope of Live Jurkat Cells and Cellular Uptake Assay according to the same protocols as mentioned in the above Example 1.

Results

1. Results of RNA Binding Specificity

Figure 5:
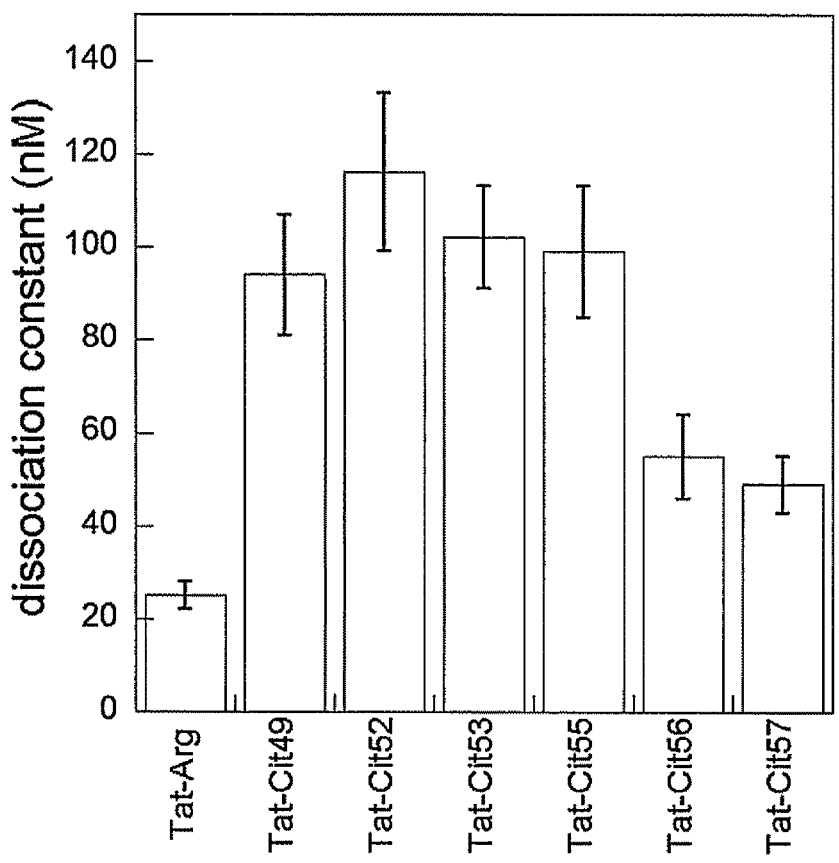
FIG. 5 illustrated binding affinity for Tat-peptide and TAR RNA determined by fluorescence anisotropy assay.

Binding affinity for Tat-peptide and TAR RNA determined by fluorescence anisotropy assay was shown in FIG. 5 and Table 2 in which the smaller K$_D$ is, the stronger the binding affinity is. FIG. 5 illustrated that all RNA virus-derived peptides (Tat-Cit49 to Tat-Cit57) exhibited the binding affinity after the charge modification in the side chains. Further, Table 2 illustrated that naturally-occurring Tat(Tat-Arg) had a greatest binding affinity to TAR-RNA, the sequence of which from strong to weak was Tat(Tat-Arg)>Cit56~Cit57>Cit49~Cit52~Cit53~Cit55. Thus, these results demonstrated that binding affinity between Tat-peptide and TAR RNA could be regulated by modifying bearing charges of peptides.

TABLE 2 results of binding affinity of Tat-peptide and TAR RNA determined by fluorescence anisotropy assay.

| name | K$_D$ (nM) |
|---|---|
| Tat-Arg | 25 ± 3 |
| Tat-Cit49 | 94 ± 13 |
| Tat-Cit52 | 116 ± 17 |
| Tat-Cit53 | 102 ± 11 |
| Tat-Cit55 | 99 ± 14 |
| Tat-Cit56 | 55 ± 9 |
| Tat-Cit57 | 49 ± 6 |

Figure 6:
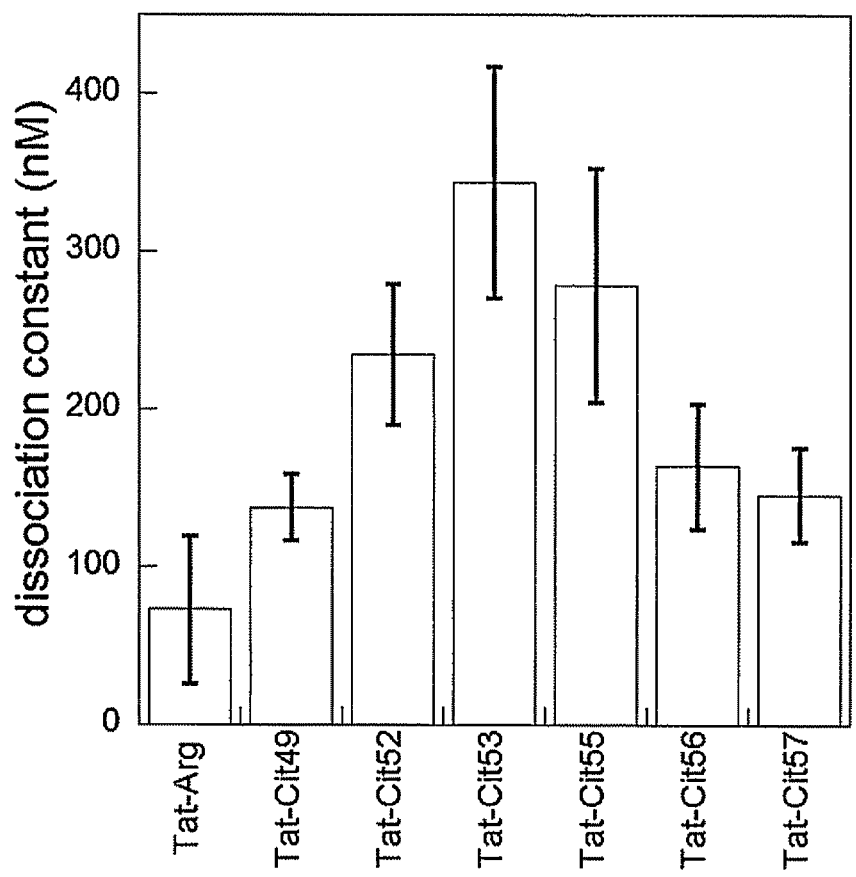
FIG. 6 illustrated the result of dissociation constant for Tat-peptide and TAR RNA determined by gel shift assay in the presence of poly(dI-dC).

Table 3 and FIG. 6 illustrated the result of the dissociation constant of Tat-peptide and TAR RNA determined by gel shift assay in the presence of poly(dI-dC) at 25° C. The studies of the binding affinity for TAR-RNA in FIG. 6 showed that replacing NH$_2$ groups in Tat(Tat-Arg) with 0 to neutralize positive charges may weaken the binding affinity for TAR-RNA.

To determine the specificity, the strength of the binding affinity was determined in the presence of competing negatively charged poly(dI-dC). The sequence of the binding affinity from strong to weak was Tat(Tat-Arg)>Cit49~Cit56~Cit57>Cit52~Cit53~Cit55. The results shown in Table 3 and FIG. 6 suggested that altering charges in Tat peptides could regulate the specificity between Tat and TAR-RNA.

TABLE 3 the result of dissociation constant of Tat-peptide and TAR RNA
determined by gel shift assay in the presence of poly(dI-dC) at 25° C.

| name | $K_D$ (nM) |
|---|---|
| Tat-Arg | 67 ± 19 |
| Tat-Cit49 | 138 ± 21 |
| Tat-Cit52 | 235 ± 45 |
| Tat-Cit53 | 344 ± 73 |
| Tat-Cit55 | 279 ± 74 |
| Tat-Cit56 | 164 ± 40 |
| Tat-Cit57 | 146 ± 30 |

2. Results of Cellular Uptake Experiments

Figure 7:
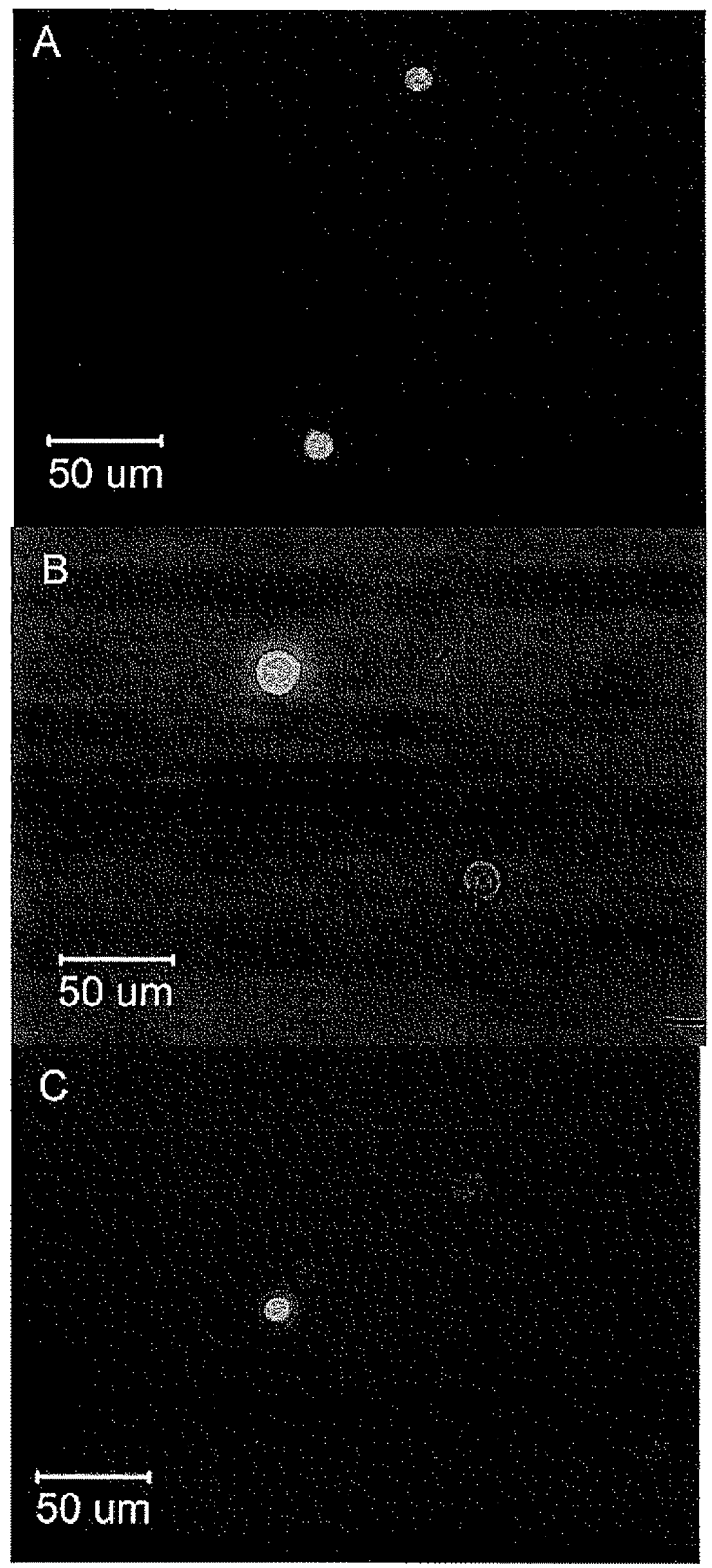
FIG. 7 illustrated fluorescence microscope images for Jurkat cells which were incubated with the 30 μM Tat derived peptide at 37° C., 5% $CO_2$ for 15 minutes and trypsinized for 10 minutes. (panel A: 6CF-Tat-Cit49; panel B: 6CF-Tat-Cit52; panel C: 6CF-Tat-Cit53; panel D: 6CF-Tat-Cit55; panel E: 6CF-Tat-Cit56; panel F: 6CF-Tat-Cit57).
Figure 7:
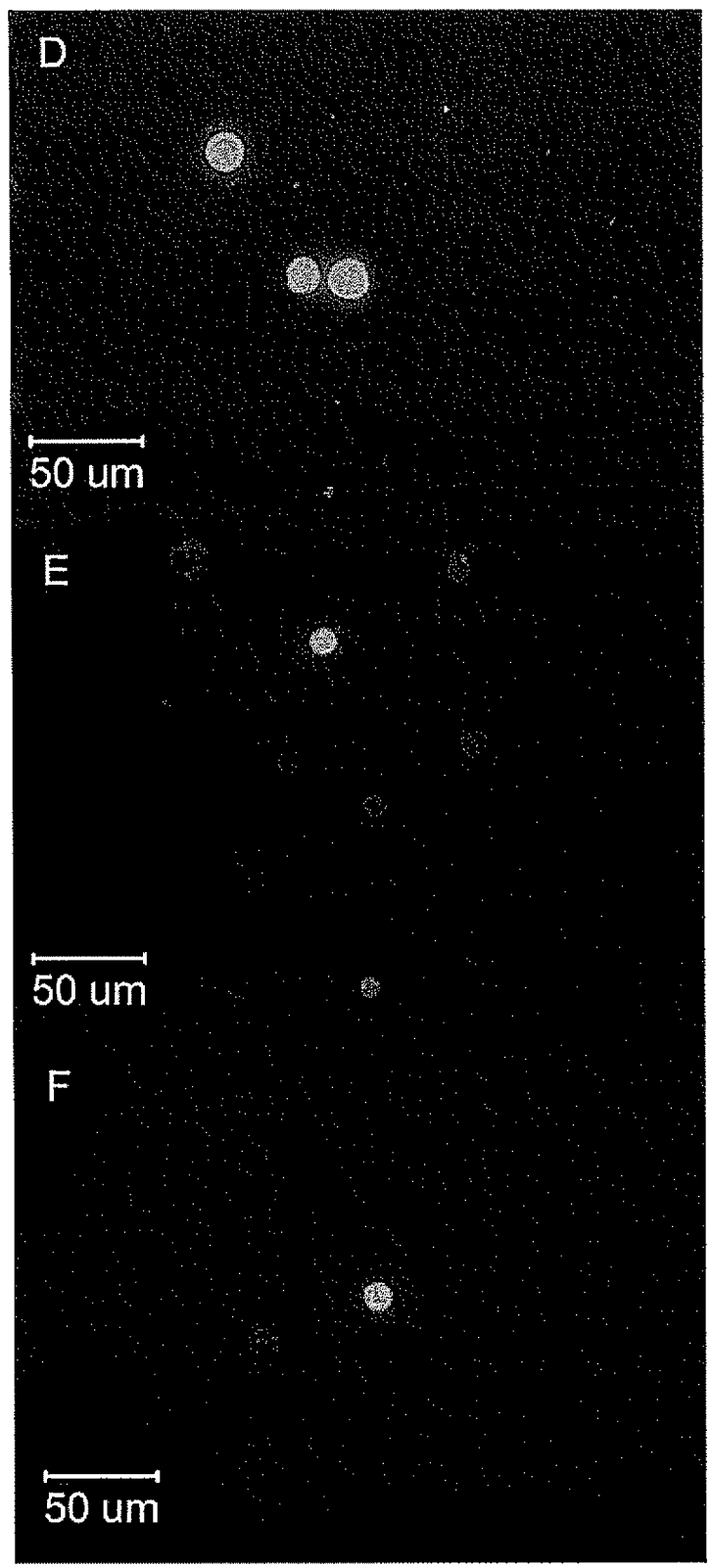

Fluorescence microscope and flow cytometry were applied to investigate the effect on cellular uptake after replacing $NH_2$ with 0 (i.e. to neutralize positive charges) in Tat peptides FIG. 7 illustrated fluorescence microscope images for Jurkat cells which were incubated with the 30 μM Tat derived peptide at 37° C., 5% $CO_2$ for 15 minutes and trypsinized for 10 minutes. (panel A: 6CF-Tat-Cit49; panel B: 6CF-Tat-Cit52; panel C: 6CF-Tat-Cit53; panel D: 6CF-Tat-Cit55; panel E: 6CF-Tat-Cit56; panel F: 6CF-Tat-Cit57). All six peptides exhibited significant cellular uptake in theses figures.

Figure 8:
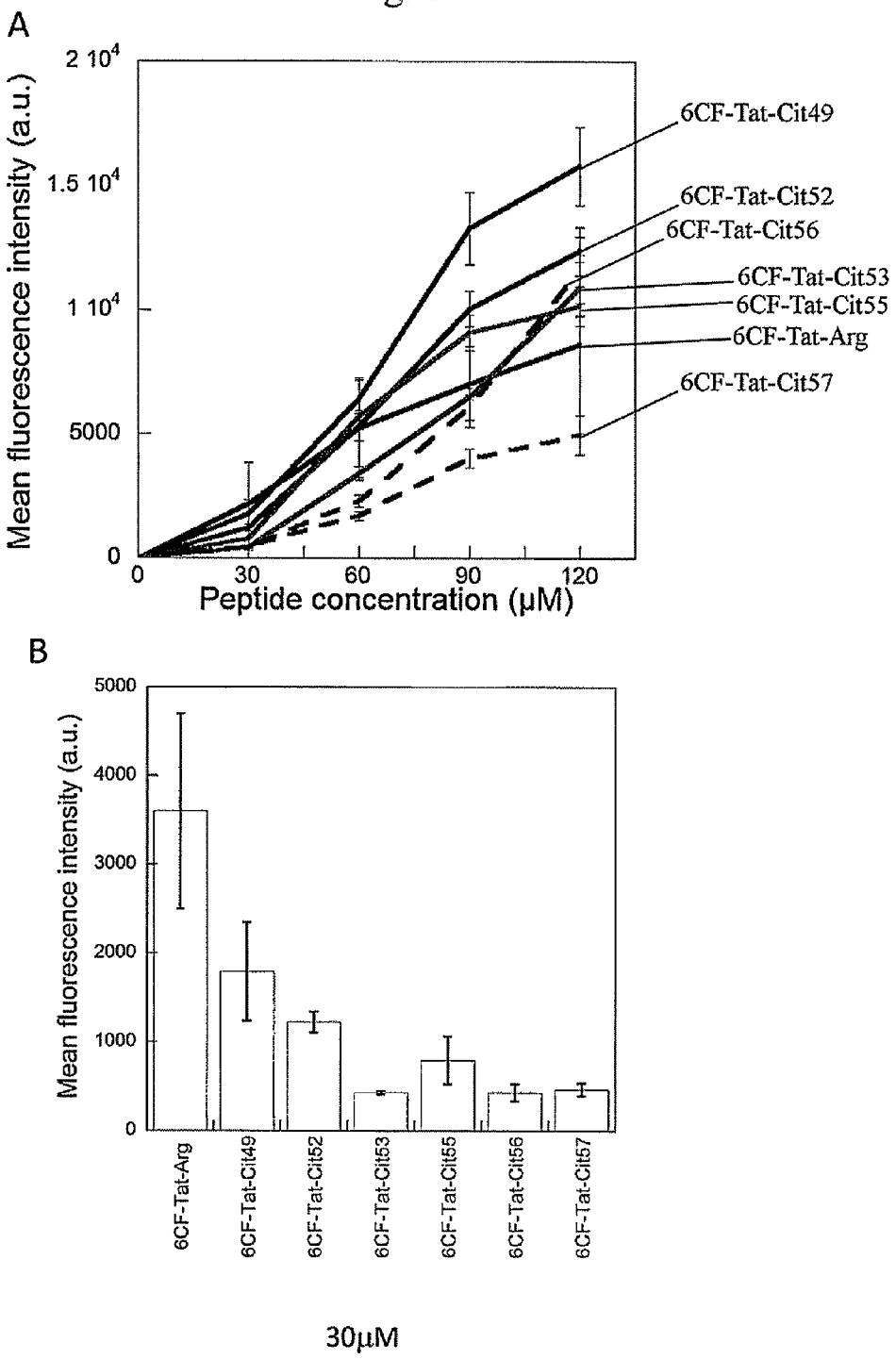
FIG. 8 illustrated the dose dependent fluorescence intensity of Jurkat cells in cellular uptake assays (panel A: the relationship between the peptide concentration and the fluorescence intensity; panel B: Mean fluorescence intensity of each peptide at 30 μM concentration; panel C: Mean fluorescence intensity of each peptide at 120 μM concentration).
Figure 8:
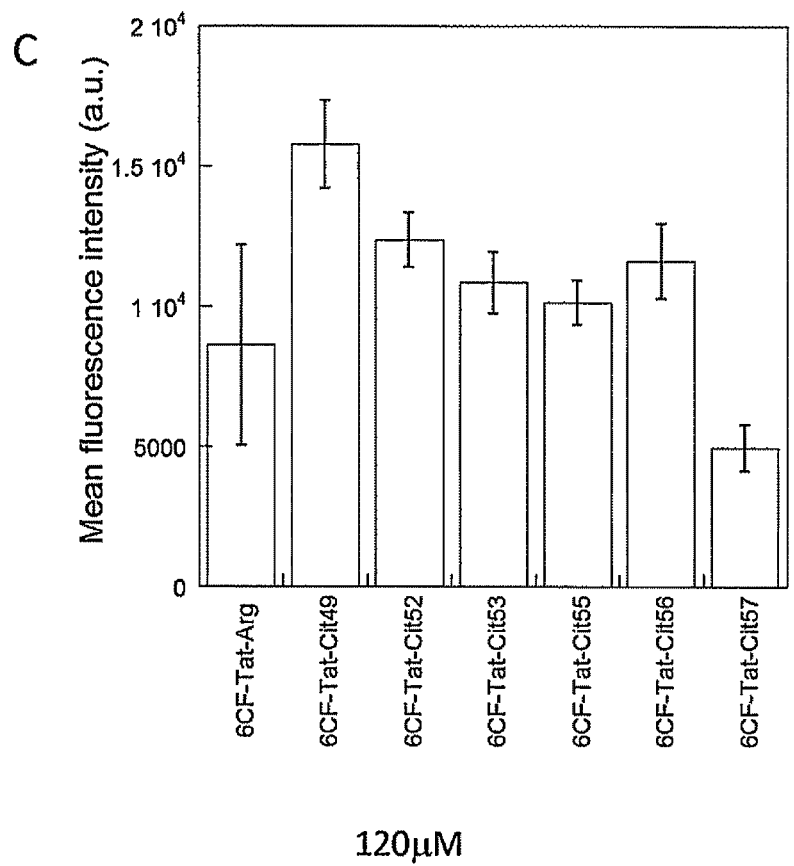

In addition, FIG. 8 illustrated the dose dependent fluorescence intensity of Jurkat cells in cellular uptake assays (panel A: the relationship between the peptide concentration and the fluorescence intensity; panel B: Mean fluorescence intensity of each peptide at 30 μM concentration; panel C: Mean fluorescence intensity of each peptide at 120 μM concentration). Table 4 illustrated the data of FIG. 8 A, showing Jurkat cells in cellular uptake assays at various concentration. FIG. 8B showed that naturally-occurring Tat(Tat-Arg) had the best cellular uptake capability in all peptides. However, when the concentration was increased up to 120 μM (FIG. 8C), the sequence of cellular uptake capability was Cit49>Tat(Tat-Arg)~Cit52~Cit53~Cit55~Cit56>Cit 57.

These results demonstrated that all modified peptides (6CF-Tat-Cit49 to 6CF-Tat-Cit57) exhibited cellular uptake capability, which may be regulated by modifying charges in Arg side chain.

Example 3

Modifying Partial Arginine Side-Chain Length in Tat(47-57) Derived Peptides to Observe Effects on RNA Binding Affinity The Peptide Preparation Example

```
(i.e. n₆ of formula (I) was 1; SEQ ID NO: 19)
Ac-Agp57-Tat(47-57)-NH₂(Ac-Tyr-Gly-Arg-Lys- Lys-Arg-Arg-Gln-Arg-Arg-Agp-NH₂)
```

This peptide was prepared by replacing Arg in the 57th position of the naturally-occurring Tat-derived peptide (SEQ ID NO.:3) with Agp ((S)-2-amino-3-guanidinopropionic acid). The preparing method was as follows:

Fmoc-PAL-PEG-PS (0.05 mmol) was swollen in N, N-dimethylformamide (DMF) for 30 minutes.

The resin was washed with DMF (5 mL, 5×1.5 min). The resin was then deprotected by 20% piperidine/DMF (5 mL, 3×8 min) and rinsed with DMF (5 mL, 5×1.5 min). The mixture of the appropriate protected amino acid (3 equivalents), HOBT (3 equivalents), and HBTU (3 equivalents) was dissolved in 1 mL DMF and DIEA (12 equivalents), and then applied to the resin. The vial was washed with DMF (2×1 mL) and applied to the resin and shaken. The coupling time depended on the kind (β-branch) and location of amino acid. Arginine was triple coupled for 25 minutes each time. The first amino acid was coupled for 8 hours, residues 2~7 for 75 minutes, residues 8~15 for 90 minutes. When the coupling was complete, the resin was washed with DMF and deblocked as described earlier. Then a mixture of acetic anhydride (95 μL, 20 equivalents) and DIEA (125 μL, 20 equivalents) was added, followed by washing the vial which was used for containing the resin with DMF (3×1 mL). The reactants were shaken for 2 hours, washed five times with DMF (5 mL, 5×1.5 min) and methanol (5 mL), and then lyophilized overnight. For Agp-containing peptides, the corresponding Dap(Mtt)-containing peptide (Ac-Dap57-Tat(47-57)-NH₂) was synthesized first. The Mtt protecting group was then removed by suspending the resin in 1% $CF_3COOH$ in $CH_2Cl_2$ (4 mL, 15×3 min) and shaking at room temperature. Deprotection was continued until the filtrate no longer appeared yellow.

TABLE 4

Mean fluorescence intensity for Tat derived peptides of Jurkat cells in cellular uptake assays.

| Peptide | Mean fluorescence intensity (a.u.) | | | |
|---|---|---|---|---|
| | 30 μM | 60 μM | 90 μM | 120 μM |
| 6CF-Tat-Arg | 2170 ± 1692 | 5258 ± 2006 | 7042 ± 1475 | 8628 ± 3585 |
| 6CF-Tat-Cit49 | 1791 ± 555 | 6452 ± 740 | 13284 ± 1441 | 15784 ± 1567 |
| 6CF-Tat-Cit52 | 1221 ± 116 | 5332 ± 612 | 10040 ± 726 | 12378 ± 972 |
| 6CF-Tat-Cit53 | 429 ± 19 | 3417 ± 288 | 6499 ± 109 | 10861 ± 1096 |
| 6CF-Tat-Cit55 | 793 ± 267 | 5750 ± 134 | 9090 ± 707 | 10152 ± 787 |
| 6CF-Tat-Cit56 | 429 ± 95 | 2305 ± 249 | 6094 ± 792 | 11617 ± 1339 |
| 6CF-Tat-Cit57 | 465 ± 72 | 1696 ± 167 | 4031 ± 377 | 4964 ± 811 |

The resin was washed with $CH_2Cl_2$ (4 mL, 5×1.5 min) and lyophilized. After removal of orthogonal protecting groups from the resin-bound protected peptides, the resin was resuspended in a solution of N,N'-di-Boc-N''-trifluoromethanesulfonylguanidine (820.9 mg, 2 mmol) and $Et_3N$ (480 μL, 6.5 mmol) in $CH_2Cl_2$. The reaction was shaken at room temperature. The reaction was microwaved once every hour (3×7 sec, 30% power). Reaction was monitored by cleaving a small amount (about 5 mg) of peptide-bound resin and analyzed by RP-HPLC. Peptides were deprotected and cleaved off the resin by treating the resin with trifluoroacetic acid (5 mL)/triisopropylsilane (250 μL) and shaken for 2 hours. The solution was then filtered through glass wool and the resin was washed with TFA (3×3 mL). The combined filtrate was evaporated by a gentle stream of $N_2$. The resulting material was washed with hexanes (3×3 mL), dissolved in water, and lyophilized. The peptide was analyzed using analytical RP-HPLC and confirmed by MALDI-TOF MS. The analytical condition of RP-HPLC was on a 250 mm $C_{18}$ column with a flow rate of 1 mL $min^{-1}$, temperature 25° C., linear 1% $min^{-1}$ gradient from 100% A to 0% A (solvent A: 99.9% water, 0.1% TFA; solvent B: 90% acetonitrile, 10% water, 0.1% TFA). Different linear gradients (solvent A: 99.9% water, 0.1% TFA; solvent B: 90% acetonitrile, 10% water, 0.1% TFA) were chosen to purify each peptide by preparative RP-HPLC equipped with either a $C_4$ or $C_{18}$ column using 10 mL/min flow rate, linear 0.5%/min gradient. Preparative RP-HPLC was performed on a Waters Breeze chromatography system using a Vydac $C_4$ and $C_{18}$ columns (22 mm diameter, 250 mm length).

Figure 9:
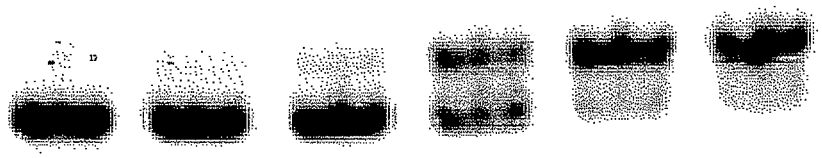
FIG. 9 illustrated the result of Ac-Agp57-Tat-$NH_2$ and 10 μg/mL poly(dI-dC) determined by gel shift assay.

The dissociation constant for Tat-peptide (Ac-Agp57-Tat-$NH_2$) and TAR RNA determined by gel shift assay (The detail method referred to Example 1 and needn't have been given herein) in the presence of 10 μg/mL poly(dI-dC). FIG. 9 illustrated the result of Ac-Agp57-Tat-$NH_2$ and 10 μg/mL poly(dI-dC) determined by gel shift assay. From FIG. 9, the determined $K_D$ of Ac-Agp57-Tat-$NH_2$ and TAR-RNA was 56±12 had no apparent difference compared with that of naturally-occurring Tat ($K_D$=67±19), suggesting that the non-naturally occurring Tat peptides which have a side-chain length of n=1 also had the binding affinity.

Conclusion: Examples of the present invention showed that altering Arg side-chain length (e.g. altering shortening Arg by one methylene to Agb in Tat-derived peptides) or charges thereof (e.g. replacing $NH_2$ with O) resulted in improvement in both bioactivities: RNA binding and cell penetration. These results suggested that introducing similar but previously non-existing building blocks such as non-natural amino acids can alter the bioactivity landscape. Furthermore, these results demonstrated that altering the Arg side-chain length affected both RNA binding, and thereby design anti-HIV therapeutics or drug delivery applications.

The above-disclosed subject matter is to be considered illustrative, and not restrictive, and the appended claims are intended to cover all such modifications, enhancements, and other embodiments, which fall within the true spirit and scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. A RNA virus-derived peptide with modified side chains, comprising the formula (I):

wherein the $n_1, n_2, n_3, n_4, n_5$ and $n_6$ are a positive integer no greater than 8, respectively;

X is NH or O;

Y, Y' and Y" are any amino acid side chain group, respectively; and the $n_1, n_2, n_3, n_4, n_5$ and $n_6$ are not 3 at the same time when X is NH.

2. The RNA virus-derived peptide of claim 1, wherein the $n_1, n_2, n_3, n_4, n_5$ and $n_6$ are 3, respectively when X is O.

3. The RNA virus-derived peptide of claim 1, wherein the RNA virus-derived peptide is a HIV virus-derived peptide.

4. The RNA virus-derived peptide of claim 3, wherein the HIV virus-derived peptide is a Tat(47-57) derived peptide.

5. The RNA virus-derived peptide of claim 1, which is Tyr-Gly-Agb-Lys-Lys-Agb-Agb-Gln-Agb-Agb-Agb-NH$_2$ (SEQ ID NO: 1), wherein the Agb is (S)-2-amino-4-guanidinobutyric acid.

6. The RNA virus-derived peptide of claim 1, which is Tyr-Gly-Agh-Lys-Lys-Agh-Agh-Gln-Agh-Agh-Agh-NH$_2$ (SEQ ID NO: 2), wherein the Agh is (S)-2-amino-6-guanidinohexanoic acid.

7. The RNA virus-derived peptides of claim 1, wherein the $n_1, n_2, n_3, n_4, n_5$ and $n_6$ are 2, respectively.

8. The RNA virus-derived peptides of claim 1, wherein the $n_1, n_2, n_3, n_4, n_5$ and $n_6$ are 4, respectively.

9. A composition comprising:

the RNA virus-derived peptide of claim 1; and a pharmaceutically acceptable adjuvant.

10. The composition of claim 9, further comprising a drug.

11. A drug delivery carrier comprising the RNA virus-derived peptide of claim 1.

* * * * *

SEQUENCE LISTING

```
<160> NUMBER OF SEQ ID NOS: 32

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X in the all positions are (S)-2-amino-4-
      guanidinobutyric acid (Agb)

<400> SEQUENCE: 1

Tyr Gly Xaa Lys Lys Xaa Xaa Gln Xaa Xaa Xaa
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X in all positions are (S)-2-amino-6-
      guanidinohexanoic acid (Agh)

<400> SEQUENCE: 2

Tyr Gly Xaa Lys Lys Xaa Xaa Gln Xaa Xaa Xaa
1               5                   10
```

```
<210> SEQ ID NO 3
<211> LENGTH: 11
<212> TYPE: PRT
<213> ORGANISM: Human immunodeficiency virus
<220> FEATURE:
<221> NAME/KEY: PEPTIDE
<222> LOCATION: (1)..(11)

<400> SEQUENCE: 3

Tyr Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the other positions are
      (S)-2-amino-6-guanidinohexanoic acid (Agh)

<400> SEQUENCE: 4

Xaa Tyr Gly Xaa Lys Lys Xaa Xaa Gln Xaa Xaa Xaa
1               5                   10

<210> SEQ ID NO 5
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein.

<400> SEQUENCE: 5

Xaa Tyr Gly Arg Lys Lys Arg Arg Gln Arg Arg Arg
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the other positions are
      (S)-2-amino-4-guanidinobutyric acid (Agb)

<400> SEQUENCE: 6

Xaa Tyr Gly Xaa Lys Lys Xaa Xaa Gln Xaa Xaa Xaa
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit
```

```
<400> SEQUENCE: 7

Tyr Gly Xaa Lys Lys Arg Arg Gln Arg Arg Arg
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit

<400> SEQUENCE: 8

Tyr Gly Arg Lys Lys Xaa Arg Gln Arg Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit

<400> SEQUENCE: 9

Tyr Gly Arg Lys Lys Arg Xaa Gln Arg Arg Arg
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit

<400> SEQUENCE: 10

Tyr Gly Arg Lys Lys Arg Arg Gln Xaa Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit

<400> SEQUENCE: 11

Tyr Gly Arg Lys Lys Arg Arg Gln Arg Xaa Arg
1               5                   10

<210> SEQ ID NO 12
<211> LENGTH: 11
<212> TYPE: PRT
<213> ORGANISM: Artificial Sequence
<220> FEATURE:
```

```
<223> OTHER INFORMATION: Synthetic peptide
<220> FEATURE:
<221> NAME/KEY: PEPTIDE
<222> LOCATION: (1)..(11)
<223> OTHER INFORMATION: X is Cit

<400> SEQUENCE: 12

Tyr Gly Arg Lys Lys Arg Arg Gln Arg Arg Xaa
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the position 4 is Cit.

<400> SEQUENCE: 13

Xaa Tyr Gly Xaa Lys Lys Arg Arg Gln Arg Arg Arg
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the position 7 is Cit.

<400> SEQUENCE: 14

Xaa Tyr Gly Arg Lys Lys Xaa Arg Gln Arg Arg Arg
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 2 is bAla which is further
      modified by 6-carboxyfluorescein; X in the position 8 is Cit.

<400> SEQUENCE: 15

Xaa Tyr Gly Arg Lys Lys Arg Xaa Gln Arg Arg Arg
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the position 10 is Cit.

<400> SEQUENCE: 16
```

-continued

Xaa Tyr Gly Arg Lys Lys Arg Arg Gln Xaa Arg Arg
1               5                   10

<210> SEQ ID NO 17
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the position 11 is Cit.

<400> SEQUENCE: 17

Xaa Tyr Gly Arg Lys Lys Arg Arg Gln Arg Xaa Arg
1               5                   10

<210> SEQ ID NO 18
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(12)
<223> OTHER INFORMATION: X in the position 1 is bAla which is further
      modified by 6-carboxyfluorescein; X in the position 12 is Cit.

<400> SEQUENCE: 18

Xaa Tyr Gly Arg Lys Lys Arg Arg Gln Arg Arg Xaa
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is (S)-2-amino-3-guanidinopropionic acid
      (Agp)

<400> SEQUENCE: 19

Tyr Gly Arg Lys Lys Arg Arg Gln Arg Arg Xaa
1               5                   10

<210> SEQ ID NO 20
<211> LENGTH: 11
<212> TYPE: PRT
<213> ORGANISM: Human immunodeficiency virus
<220> FEATURE:
<221> NAME/KEY: PEPTIDE
<222> LOCATION: (1)..(11)

<400> SEQUENCE: 20

Tyr Gly Arg Lys Lys Arg Pro Gln Arg Arg Arg
1               5                   10

<210> SEQ ID NO 21
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE

```
<222> LOCATION: (1)..(11)
<223> OTHER INFORMATION: X is Cit and Tyr in the position 1 is further
      protected by Fmoc

<400> SEQUENCE: 21

Tyr Gly Xaa Lys Lys Arg Arg Gln Arg Arg Arg
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 22

Tyr Gly Arg Lys Lys Xaa Arg Gln Arg Arg Arg
1               5                   10

<210> SEQ ID NO 23
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 23

Tyr Gly Arg Lys Lys Arg Xaa Gln Arg Arg Arg
1               5                   10

<210> SEQ ID NO 24
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 24

Tyr Gly Arg Lys Lys Arg Arg Gln Xaa Arg Arg
1               5                   10

<210> SEQ ID NO 25
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 25

Tyr Gly Arg Lys Lys Arg Arg Gln Arg Xaa Arg
1               5                   10
```

<210> SEQ ID NO 26
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 26

Tyr Gly Arg Lys Lys Arg Arg Gln Arg Arg Xaa
1               5                   10

<210> SEQ ID NO 27
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 27

Tyr Gly Xaa Lys Lys Arg Arg Gln Arg Arg Arg
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 28

Tyr Gly Arg Lys Lys Xaa Arg Gln Arg Arg Arg
1               5                   10

<210> SEQ ID NO 29
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 29

Tyr Gly Arg Lys Lys Arg Xaa Gln Arg Arg Arg
1               5                   10

<210> SEQ ID NO 30
<211> LENGTH: 11
<212> TYPE: PRT
<213> ORGANISM: Artificial Sequence
<220> FEATURE:
<223> OTHER INFORMATION: Synthetic peptide

```
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 30

Tyr Gly Arg Lys Lys Arg Arg Gln Xaa Arg Arg
1               5                   10

<210> SEQ ID NO 31
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 31

Tyr Gly Arg Lys Lys Arg Arg Gln Arg Xaa Arg
1               5                   10

<210> SEQ ID NO 32
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: PEPTIDE
<222> LOCATION: (1)..(11)
<223> OTHER INFORMATION: X is Cit and Tyr in the position 1 is further
      protected by Fmoc

<400> SEQUENCE: 32

Tyr Gly Arg Lys Lys Arg Arg Gln Arg Arg Xaa
1               5                   10
```